United States Patent
Rezaei et al.

(10) Patent No.: US 11,103,505 B2
(45) Date of Patent: Aug. 31, 2021

(54) FORMULATIONS OF A COMPOUND MODULATING KINASES

(71) Applicant: Plexxikon Inc., Berkeley, CA (US)

(72) Inventors: Hamid Rezaei, Berkeley, CA (US); Marika Nespi, Berkeley, CA (US); Prabha N. Ibrahim, Mountain View, CA (US); Gary Conard Visor, Castro Valley, CA (US)

(73) Assignee: Plexxikon Inc., South San Francisco, CA (US)

(*) Notice: Subject to any disclaimer, the term of this patent is extended or adjusted under 35 U.S.C. 154(b) by 0 days.

(21) Appl. No.: 16/172,573

(22) Filed: Oct. 26, 2018

(65) Prior Publication Data

US 2019/0125747 A1 May 2, 2019

Related U.S. Application Data

(60) Provisional application No. 62/578,334, filed on Oct. 27, 2017.

(51) Int. Cl.

| | | |
|---|---|---|
| *A61K 31/506* | (2006.01) | |
| *A61K 31/79* | (2006.01) | |
| *A61K 45/06* | (2006.01) | |
| *A61K 47/20* | (2006.01) | |
| *A61K 9/20* | (2006.01) | |
| *A61P 35/02* | (2006.01) | |
| *A61K 31/5377* | (2006.01) | |
| *A61P 35/04* | (2006.01) | |
| *A61P 35/00* | (2006.01) | |
| *A61K 9/16* | (2006.01) | |
| *A61K 9/14* | (2006.01) | |
| *A61K 9/10* | (2006.01) | |

(52) U.S. Cl.
CPC ............ *A61K 31/506* (2013.01); *A61K 9/146* (2013.01); *A61K 9/1652* (2013.01); *A61K 9/2027* (2013.01); *A61K 9/2031* (2013.01); *A61K 9/2054* (2013.01); *A61K 9/2095* (2013.01); *A61K 31/5377* (2013.01); *A61K 31/79* (2013.01); *A61K 45/06* (2013.01); *A61K 47/20* (2013.01); *A61P 35/00* (2018.01); *A61P 35/02* (2018.01); *A61P 35/04* (2018.01); *A61K 9/10* (2013.01)

(58) Field of Classification Search
CPC .......... A61P 35/00; A61P 35/02; A61P 35/04; A61K 47/20; A61K 31/5377; A61K 9/1652; A61K 9/146; A61K 45/06; A61K 31/79; A61K 31/506; A61K 9/2054; A61K 9/2031; A61K 9/2027; A61K 9/2095; A61K 9/10; A61K 2300/00
See application file for complete search history.

(56) References Cited

U.S. PATENT DOCUMENTS

| | | |
|---|---|---|
| 7,202,266 B2 | 4/2007 | Arnold et al. |
| 7,348,338 B2 | 3/2008 | Arnold et al. |
| 7,476,746 B2 | 1/2009 | Artis et al. |
| 7,491,831 B2 | 2/2009 | Artis et al. |
| 7,498,342 B2 | 3/2009 | Ibrahim et al. |
| 7,504,509 B2 | 3/2009 | Ibrahim et al. |
| 7,517,970 B2 | 4/2009 | West et al. |
| 7,531,568 B2 | 5/2009 | Lin et al. |
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,759,475 B2 | 7/2010 | West |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,872,018 B2 | 1/2011 | Ibrahim et al. |
| 7,893,075 B2 | 2/2011 | Zhang et al. |
| 7,947,708 B2 | 5/2011 | Ibrahim et al. |
| 8,053,463 B2 | 11/2011 | Lin et al. |

(Continued)

FOREIGN PATENT DOCUMENTS

| | | |
|---|---|---|
| WO | WO 2007/013896 | 2/2007 |
| WO | WO 2010/111527 | 9/2010 |

(Continued)

OTHER PUBLICATIONS

TargetMol. "PLX8394". Retrieved May 21, 2019. Retrieved online <URL: https://www.targetmol.com/compound/PLX8394; pp. 1-3. (Year: 2019).*
U.S. Appl. No. 16/058,945, filed Aug. 8, 2018, Wu.
U.S. Appl. No. 16/109,199, filed Aug. 22, 2018, Wu.
U.S. Appl. No. 16/123,612, filed Sep. 6, 2018, Desai et al.
U.S. Appl. No. 16/148,244, filed Oct. 1, 2018, Zhang et al.
U.S. Appl. No. 16/158,107, filed Oct. 11, 2018, Ibrahim et al.

(Continued)

*Primary Examiner* — Doan T Phan
(74) *Attorney, Agent, or Firm* — Sheppard Mullin Richter & Hampton LLP

(57) ABSTRACT

Provided are solid dispersions of Compound I having the formula:

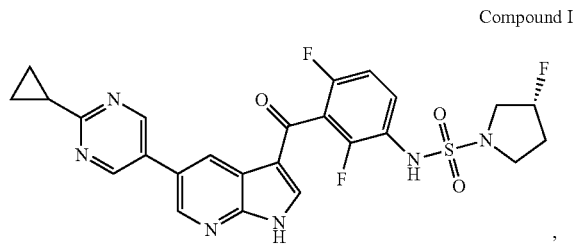

Compound I wherein Compound I is substantially amorphous, methods of manufacturing said solid dispersions, and methods of using said solid dispersions.

19 Claims, 2 Drawing Sheets

(56) References Cited

U.S. PATENT DOCUMENTS

| | | | |
|---|---|---|---|
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Zhang et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,470,821 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Diodone et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,096,593 B2 | 8/2015 | Zhang et al. |
| 9,150,570 B2 | 10/2015 | Ibrahim et al. |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,676,748 B2 | 6/2017 | Wu et al. |
| 9,682,981 B2 | 6/2017 | Zhang et al. |
| 9,695,169 B2 | 7/2017 | Ibrahim |
| 9,718,847 B2 | 8/2017 | Zhang et al. |
| 9,730,918 B2 | 8/2017 | Bollag et al. |
| 9,745,298 B2 | 8/2017 | Ibrahim et al. |
| 9,771,363 B2 | 9/2017 | Ibrahim et al. |
| 9,771,369 B2 | 9/2017 | Lin et al. |
| 9,776,998 B2 | 10/2017 | Ibrahim et al. |
| 9,802,932 B2 | 10/2017 | Ibrahim et al. |
| 9,814,714 B2 | 11/2017 | Ibrahim et al. |
| 9,822,109 B2 | 11/2017 | Zhang et al. |
| 9,844,539 B2 | 12/2017 | Wu et al. |
| 9,856,259 B2 | 1/2018 | Shi et al. |
| 9,873,700 B2 | 1/2018 | Zhang et al. |
| 9,938,273 B2 | 4/2018 | Wu et al. |
| 9,975,894 B2 | 5/2018 | Ibrahim et al. |
| 9,994,567 B2 | 6/2018 | Ibrahim et al. |
| 10,040,792 B2 | 8/2018 | Ibrahim et al. |
| 10,123,998 B2 | 11/2018 | Bollag et al. |
| 10,160,747 B2 | 12/2018 | Lin et al. |
| 10,160,755 B2 | 12/2018 | Lin et al. |
| 10,189,833 B2 | 1/2019 | Ibrahim et al. |
| 10,227,357 B2 | 3/2019 | Lin et al. |
| 10,301,280 B2 | 5/2019 | Wu et al. |
| 10,316,032 B2 | 6/2019 | Ibrahim et al. |
| 10,370,374 B2 | 8/2019 | Ibrahim et al. |
| 2004/0142864 A1 | 7/2004 | Bremer et al. |
| 2004/0171062 A1 | 9/2004 | Hirth et al. |
| 2005/0048573 A1 | 3/2005 | Artis et al. |
| 2005/0079548 A1 | 4/2005 | Artis et al. |
| 2005/0164300 A1 | 7/2005 | Artis et al. |
| 2005/0170431 A1 | 8/2005 | Ibrahim et al. |
| 2006/0058339 A1 | 3/2006 | Ibrahim et al. |
| 2006/0135540 A1 | 6/2006 | Lin et al. |
| 2006/0160135 A1 | 7/2006 | Wang et al. |
| 2007/0066641 A1 | 3/2007 | Ibrahim et al. |
| 2007/0072904 A1 | 3/2007 | Lin et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2010/0190777 A1 | 7/2010 | Wu et al. |
| 2011/0092538 A1 | 4/2011 | Spevak et al. |
| 2011/0112127 A1 | 5/2011 | Zhang et al. |
| 2011/0166174 A1 | 7/2011 | Ibrahim et al. |
| 2011/0183988 A1 | 7/2011 | Ibrahim et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0102691 A1* | 4/2013 | Miller .................... A61K 9/146 514/781 |
| 2013/0237531 A1 | 9/2013 | Wu et al. |
| 2013/0261117 A1 | 10/2013 | Ibrahim et al. |
| 2013/0303534 A1 | 11/2013 | Ibrahim et al. |
| 2014/0038948 A1 | 2/2014 | Wu et al. |
| 2014/0128373 A1* | 5/2014 | Ibrahim ............... C07D 471/04 514/210.21 |
| 2014/0128390 A1 | 5/2014 | Lin et al. |
| 2014/0303121 A1 | 10/2014 | Zhang et al. |
| 2014/0303187 A1 | 10/2014 | Wu et al. |
| 2015/0290205 A1 | 10/2015 | Ibrahim et al. |
| 2016/0176865 A1 | 6/2016 | Ibrahim et al. |
| 2016/0340357 A1 | 11/2016 | Ibrahim et al. |
| 2017/0029413 A1 | 2/2017 | Holladay et al. |
| 2017/0157120 A1 | 6/2017 | Ibrahim et al. |
| 2017/0247370 A1 | 8/2017 | Zhang et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1 | 12/2017 | Wu et al. |
| 2017/0362231 A1 | 12/2017 | Ibrahim et al. |
| 2018/0002332 A1 | 1/2018 | Ibrahim et al. |
| 2018/0030051 A1 | 2/2018 | Ibrahim et al. |
| 2018/0055828 A1 | 3/2018 | Bollag |
| 2018/0072722 A1 | 3/2018 | Zhang et al. |
| 2018/0099939 A1 | 4/2018 | Zhang et al. |
| 2018/0099975 A1 | 4/2018 | Zhang et al. |
| 2018/0111929 A1 | 4/2018 | Ibrahim |
| 2018/0111930 A1 | 4/2018 | Desai |
| 2018/0215763 A1 | 8/2018 | Wu et al. |
| 2018/0228826 A1* | 8/2018 | Harris .................... A61K 9/145 |
| 2018/0265508 A1 | 9/2018 | Lin |
| 2018/0305358 A1 | 10/2018 | Ibrahim et al. |
| 2018/0327403 A1 | 11/2018 | Ibrahim et al. |
| 2018/0354946 A1 | 12/2018 | Zhang et al. |
| 2019/0031654 A1 | 1/2019 | Ibrahim et al. |
| 2019/0119273 A1 | 4/2019 | Ibrahim et al. |
| 2019/0161484 A1 | 5/2019 | Ibrahim et al. |
| 2019/0209536 A1 | 7/2019 | Wu et al. |
| 2019/0241557 A1 | 8/2019 | Desai et al. |
| 2019/0263800 A1 | 8/2019 | Zhang et al. |
| 2020/0299293 A1 | 9/2020 | Ibrahim et al. |
| 2020/0339571 A1 | 10/2020 | Ibrahim et al. |

FOREIGN PATENT DOCUMENTS

| | | | |
|---|---|---|---|
| WO | WO 2010/129467 | 11/2010 | |
| WO | WO 2012/109075 | 8/2012 | |
| WO | WO-2016105670 A1 * | 6/2016 | ............ A61K 45/06 |
| WO | WO 2016/191296 | 12/2016 | |
| WO | WO-2016193860 A1 * | 12/2016 | ............ A61K 47/12 |
| WO | WO-2017023714 A1 * | 2/2017 | ............ A61K 9/145 |

OTHER PUBLICATIONS

U.S. Appl. No. 16/172,573, filed Oct. 26, 2018, Rezaei et al.
U.S. Appl. No. 16/219,730, filed Dec. 13, 2018, Ibrahim et al.
International Search Report and Written Opinion for PCT/US2018/057797 dated Jan. 29, 2019, 16 pages.
Okimoto et al., "Preclinical efficacy of a RAF inhibitor that evades paradoxical MAPK pathway activation in protein kinase BRAF-mutant lung cancer", Proceedings of the National Academy of Sciences of the United States of America, vol. 113, No. 47, Nov. 22, 2016, pp. 13456-13461.

(56) References Cited

OTHER PUBLICATIONS

Dhirendra K et al., "Solid dispersions: a review", Pakistan Journal of Pharmaceutical Sciences, Faculty of Pharmacy, University of Karachi, PK, vol. 22. No. 2, 1 Apr. 2009, p. 234-246.
Vasconcelos et al., "Solid dispersions a strategy to improve oral bioavailability of poor water soluble drug", Drug Discovery Today, vol. 12, Jan. 1, 2012, pp. 1068-1075.
U.S. Appl. No. 16/358,608, filed Mar. 19, 2019, Zhang et al.
U.S. Appl. No. 16/400,801, filed May 1, 2019, Ibrahim et al.
U.S. Appl. No. 16/441,610, filed Jun. 14, 2019, Ibrahim et al.
U.S. Appl. No. 16/510,617, filed Jul. 12, 2019, Ibrahim et al.
U.S. Appl. No. 16/510,757, filed Jul. 12, 2019, Ibrahim et al.
U.S. Appl. No. 16/510,764, filed Jul. 12, 2019, Ibrahim et al.
U.S. Appl. No. 16/563,656, filed Sep. 6, 2019, Zhang et al.
U.S. Appl. No. 16/687,015, filed Nov. 18, 2019, Zhang et al.
U.S. Appl. No. 16/684,198, filed Nov. 14, 2019, Desai et al.
U.S. Appl. No. 16/706,497, filed Dec. 6, 2019, Ibrahim et al.
U.S. Appl. No. 16/749,893, filed Jan. 22, 2020, Ibrahim et al.
U.S. Appl. No. 16/814,632, filed Mar. 10, 2020, Wu et al.
U.S. Appl. No. 16/843,700, filed Apr. 8, 2020, Spevak.
U.S. Appl. No. 16/854,646, filed Apr. 21, 2020, Zhang et al.
U.S. Appl. No. 16/909,315, filed Jun. 23, 2020, Zhang et al.
U.S. Appl. No. 16/916,796, filed Jun. 30, 2020, Desai et al.
U.S. Appl. No. 16/930,823, filed Jul. 16, 2020, Ibrahim et al.
U.S. Appl. No. 17/018,986, filed Sep. 11, 2020, Ibrahim et al.
U.S. Appl. No. 17/077,764, filed Oct. 22, 2020, Wu et al.
U.S. Appl. No. 17/112,745, filed Dec. 4, 2020, Vander Wal et al.
U.S. Appl. No. 17/121,484, filed Dec. 14, 2020, Ibrahim et al.

\* cited by examiner

Figure 1: Process Flow Diagram for Manufacture Solid Dispersion of Compound I Tablets made by Hot Melt Extrusion
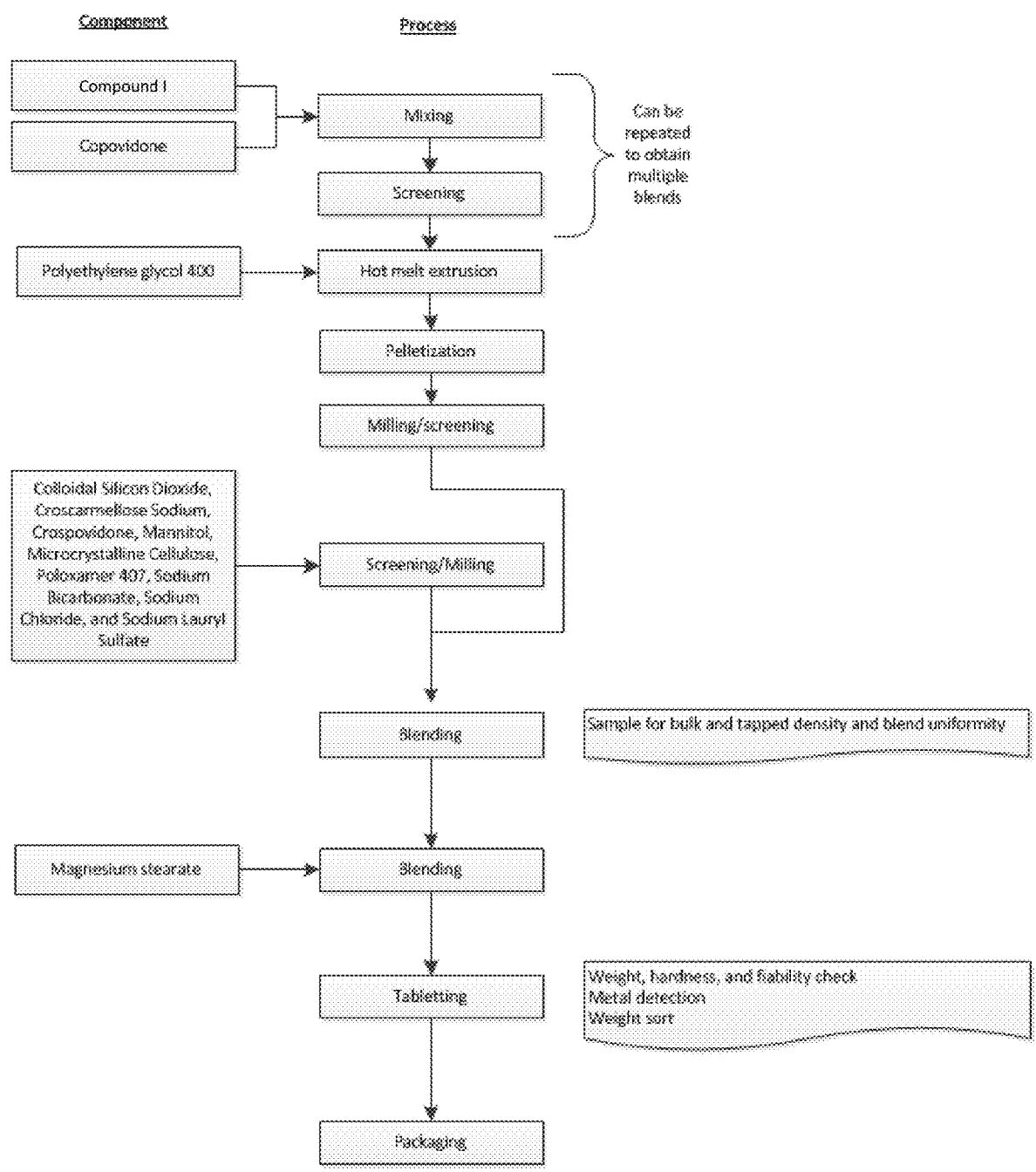

Figure 2: Process Flow Diagram for Manufacture Solid Dispersion of Compound I Tablets made by Spray Dry Dispersion
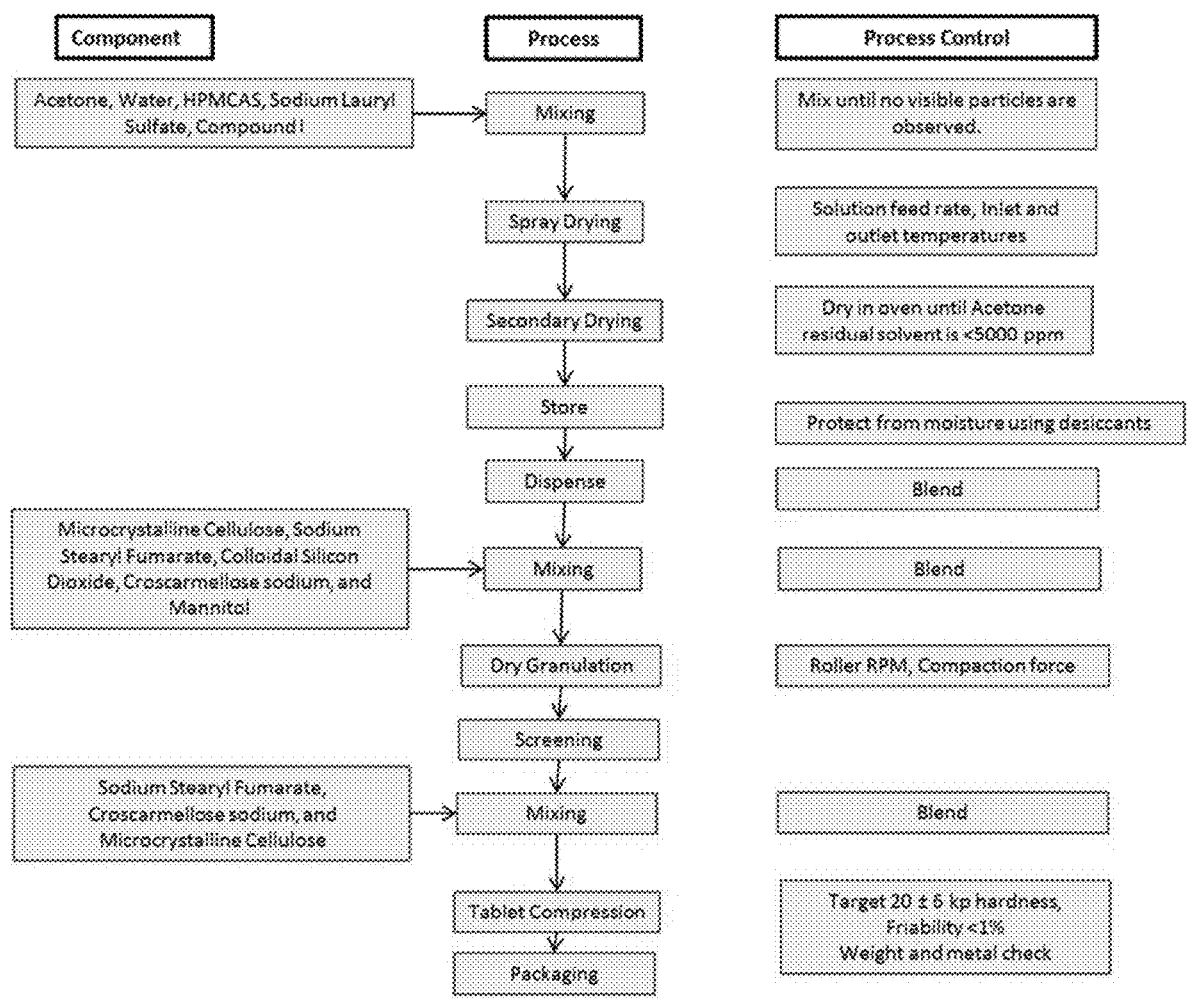

FORMULATIONS OF A COMPOUND MODULATING KINASES

CROSS-REFERENCE TO RELATED APPLICATIONS

This application claims the benefit under 35 U.S.C. § 119(e) of U.S. Provisional Application No. 62/578,334, filed Oct. 27, 2017, which is hereby incorporated by reference in its entirety.

FIELD

Disclosed are new compositions of biologically active compounds that are useful for treating diseases and methods of making such compositions.

BACKGROUND (R)-N-(3-(5-(2-cyclopropylpyrimidin-5-yl)-1H-pyrrolo [2,3-b]pyridine-3-carbonyl)-2,4-difluorophenyl)-3-fluoropyrrolidine-1-sulfonamide is a potent inhibitor of mutated forms of BRAF and can be useful for treatment of BRAF mediated diseases, such as metastatic melanoma, thyroid cancers and colorectal cancers. The compound and its synthesis have been described in WO 2012/109075 and WO 2016/191303. There remains interest in developing efficacious and safe formulations for this and other related biologically active molecules.

SUMMARY

The present disclosure relates to solid dispersions comprising Compound I having the formula:

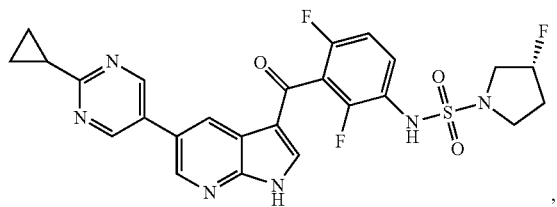

Compound I wherein Compound I is substantially amorphous.

In another embodiment, the solid dispersion of this disclosure further comprises one or more excipients.

In another embodiment, the solid dispersion of this disclosure further comprises one or more solubilizing agents.

In another embodiment of the solid dispersion of this disclosure, Compound I is molecularly dispersed within a polymer matrix formed by hydroxypropylmethyl cellulose acetate succinate (HPMCAS) in its solid state.

The present disclosure also relates to methods of making the solid dispersions of this disclosure.

The present disclosure also relates to solid dispersions made by the methods of this disclosure.

The present disclosure also relates to methods of treating subjects with a disease or condition mediated by mutant BRAF (including BRAF V600E), comprising administering a therapeutically effective amount of the solid dispersions of this disclosure to said subjects.

The present disclosure also relates to methods of treating subjects of a disease or condition mediated by mutant BRAF (including BRAF V600E), comprising administering any of the solid dispersions of this disclosure in combination with one or more CYP inhibitors (including CYP3A4 inhibitors) to said subjects.

Additional aspects and embodiments will be apparent from the following Detailed Description and from the claims.

BRIEF DESCRIPTION OF THE DRAWINGS

FIG. 1 is a process flow diagram for manufacturing a solid dispersion of amorphous Compound I by hot melt extrusion.

FIG. 2 is a process flow diagram for manufacturing a solid dispersion of amorphous Compound I by spray dry dispersion.

DETAILED DESCRIPTION

Definitions

As used herein the following definitions apply unless clearly indicated otherwise.

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

"BRAF" is a human gene that encodes a protein kinase called BRAF. BRAF mutated related disease can be BRAF V600 mutations and non-V600 mutations. The BRAF V600 mutation results in an amino acid substitution at position 600 (Valine) in BRAF.

As used herein, the terms "treat," "treating," "therapy," "therapies," and like terms refer to the administration of material, e.g., any one or more compound(s), as described herein in an amount effective to prevent, alleviate, or ameliorate one or more symptoms of a disease or condition, i.e., indication, and/or to prolong the survival of the subject being treated.

As used herein, the term "capsule formulation" refers to a capsule of any of the solid dispersions in this disclosure.

As used herein, the term "tablet formulation" refers to a tablet of any of the solid dispersions in this disclosure.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

As used herein, the term "about" used in the context of quantitative measurements means the indicated amount 10%. For example, "about 2:8" would mean 1.8-2.2:7.2-8.8.

As used herein, the term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (glass transition).

As used herein, the term "substantially amorphous" as used herein is intended to mean that greater than 60%; or greater than 65%; or greater than 70%; or greater than 75%; or greater than 80%; or greater than 85%; or greater than 90%; or greater than 95%; or greater than 99% of the compound present in a composition is in amorphous form. "Substantially amorphous" can also refer to material which has no more than about 20% crystallinity, or no more than about 10% crystallinity; or no more than about 5% crystallinity; or no more than about 2% crystallinity; or no more than about 1% crystallinity.

As used herein, the term "solid dispersion" means any solid composition having at least two components. In certain embodiments, a solid dispersion as disclosed herein includes an active ingredient (for example, Compound 1); preferably dispersed among at least one other component, for example a polymer such as HPMCAS. In certain embodiments, a solid dispersion as disclosed herein is a pharmaceutical dispersion that includes at least one pharmaceutically or biologically active ingredient (for example Compound 1). In some embodiments, a solid dispersion includes Compound I molecularly dispersed with a polymer. Preferably the solid dispersion exists as a one phase system.

As used herein, the term "crystalline" as used herein refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (melting point).

As used herein, the term "binder" as used herein refers to any pharmaceutically acceptable film which can be used to bind together the active and inert components of the carrier together to maintain cohesive and discrete portions. Non-limiting examples of binders include hydroxypropylcellulose, hydroxypropylmethylcellulose, povidone, copovidone, ethyl cellulose and combinations thereof.

As used herein, the term "disintegrant" as used herein refers to a substance which, upon addition to a solid preparation, facilitates its break-up or disintegration after administration and permits the release of an active ingredient as efficiently as possible to allow for its rapid dissolution. Non-limiting examples of disintegrants include sodium starch glycolate, croscarmellose sodium, crospovidone modified corn starch and combinations thereof.

As used herein, the term "lubricant" as used herein refers to an excipient which is added to a powder blend to prevent the compacted powder mass from sticking to the equipment during the tableting or encapsulation process. It aids the ejection of the tablet form the dies, and can improve powder flow. Non-limiting examples of lubricants include magnesium stearate, stearic acid, silica, mineral oil and combinations thereof.

As used herein, the term "glidant" as used herein refers to agents used in tablet and capsule formulations to improve flow-properties during tablet compression and to produce an anti-caking effect. Non-limiting examples of glidants include colloidal silicon dioxide, cellulose, magnesium oxide and combinations thereof.

As used herein, the term "% w/w" as used herein refers to the weight of a component based on the total weight of a composition comprising the component. For example, if component A is present in an amount of 50% w/w in a 100 mg composition, component A is present in an amount of 50 mg.

As used herein, the term "surfactant" as used herein refers to a substance that lowers the surface tension between a liquid and a solid that could improve the wetting of the active agent or improve the solubility of the active agent. Non-limiting examples of surfactants include poloxamer 407 and sodium lauryl sulfate.

As used herein, the term "solubilizing agent" as used herein refers to a substance capable of increasing the solubility of the active agent. Non-limiting examples of solubilizing agents include polyethylene glycol and copovidone.

As used herein, the term "osmogen" as used herein refers to a water soluble component which preferentially draws water into the tablet core for the purposes of distributing the water throughout the core, so that the active ingredient contained in the core may be released. Non-limiting examples of osmogens include sodium chloride and potassium chloride.

As used herein, the term "molecularly dispersed" refers to the random distribution of a compound (e.g. Compound I with a polymer. In certain embodiments, the compound is present in the polymer in a final state of subdivision. See, e.g., M. G. Vachon et al., *J Microencapsulation* 14:281-301 (1997) and Vandelli et al., *J Microencapsulation*, 10: 55-65 (1993). In some embodiments, a compound (for example, Compound I) may be dispersed within a matrix formed by the polymer in its solid state such that the compound is immobilized in its amorphous form. Whether a compound is molecularly dispersed in a polymer may be evidenced in a variety of ways, e.g., by the resulting solid molecular complex having a single glass transition temperature.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. In certain embodiments, a "therapeutically-effective amount" of Compound I refers to such dosages and/or administration for such periods of time necessary to inhibit mutant BRAF kinases, such as BRAF V600E. Moreover, a therapeutically effective amount may be one in which the overall therapeutically-beneficial effects outweigh the toxic or undesirable side effects. A therapeutically-effective amount of Compound I may vary according to disease state, age and weight of the subject being treated. Thus, dosage regimens are typically adjusted to the individual requirements in each particular case and are within the skill in the art. In certain embodiments, an appropriate daily dose for administration of Compound I to an adult human may be from about 50 mg to about 3200 mg; or from about 75 mg to about 2000 mg, although the upper and lower limits may be exceeded when indicated. A daily dosage of Compound I can be administered as a single dose, in divided doses, or, for parenteral administration, it may be given as subcutaneous injection.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

As used herein, the term "mix" or "blend" is interchangeable and means to combine two or substances.

Compositions of this disclosure can be used for oral administration to subjects for treating disease and conditions modulated by BRAF and mutated forms of BRAF mediated diseases. In certain embodiments, the compositions of this disclosure have improved bioavailability.

Solid Dispersions

Embodiment 1 relates to a solid dispersion comprising Compound I having the formula:

Compound I

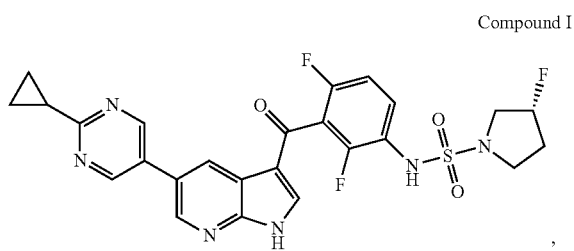 [SMILES: O=C(c1c(F)ccc(NS(=O)(=O)N2CC[C@@H](F)C2)c1F)c1c[nH]c2ncc(-c3cnc(C4CC4)nc3)cc12]

wherein Compound I is substantially amorphous.

Compound I is described in U.S. Pat. Pub. No. 2014/0128373. Compound I is a very potent mutant BRAF kinase inhibitor (also referred to herein as mutant BRAF), including BRAF V600E, and is also a particularly strong paradox breaker. Compound I does not activate the MAPK pathway which is typical of the first generation BRAF V600E mutant inhibitors.

Compound I is therefore highly advantageous in this respect, and it has been tested and proven to be potentially useful for various indications as described in U.S. Pat. Pub. No. 2016/0339025 A1.

Embodiment 2 relates to the solid dispersion according to Embodiment 1, wherein Compound I is molecularly dispersed within a polymer matrix formed by hydroxypropylmethyl cellulose acetate succinate (HPMCAS) in its solid state.

Embodiment 3 relates to the solid dispersion according to Embodiment 2, wherein the HPMCAS is HPMCAS-LF, HPMCAS-MF, HPMCAS-HF, HPMCAS-LG, HPMCAS-MG, or HPMCAS-HG.

Embodiment 4 relates to the solid dispersion according to Embodiment 3, wherein the HPMCAS is HPMCAS-HG.

Embodiment 5 relates to the solid dispersion according to any one of Embodiments 2-4 wherein the weight ratio of Compound I to HPMCAS within the solid dispersion ranges from about 1:1 to about 1:4.

Embodiment 6 relates to the solid dispersion according to any one of Embodiments 2-5 wherein the weight ratio of Compound I to HPMCAS within the solid dispersion ranges from about 1:2.5 to about 1:3.5.

Embodiment 7 relates to the solid dispersion according to any one of Embodiments 2-6, wherein the weight ratio of Compound I to HPMCAS within the solid dispersion ranges from about 1:2.6 to about 1:2.9.

Embodiment 8 relates to the solid dispersion according to any one of Embodiments 2-7, further comprising one or more surfactants.

Embodiment 9 relates to the solid dispersion according Embodiment 8, wherein the one or more surfactants is sodium lauryl sulfate (SLS).

Embodiment 10 relates to the solid dispersion according to any one of Embodiments 8 or 9, wherein Compound I ranges from about 15% w/w to about 35% w/w; HPMCAS ranges from about 50% w/w to about 85% w/w; and the one or more surfactants range from about 1% w/w to about 10% w/w.

Embodiment 11 relates to the solid dispersion according to any one of Embodiments 8-10, wherein Compound I ranges from about 20% w/w to about 30% w/w; HPMCAS ranges from about 60% w/w to about 80% w/w; and the one or more surfactants range from about 3% w/w to about 7% w/w.

Embodiment 12 relates to the solid dispersion according to any one of Embodiments 8-11, wherein Compound I ranges from about 22% w/w to about 28% w/w; HPMCAS ranges from about 65% w/w to about 75% w/w; and the one or more surfactants range from about 4% w/w to about 6% w/w.

Embodiment 13 relates to the solid dispersion according to any one of Embodiments 8-12, wherein Compound I is about 25% w/w; HPMCAS is about 70% w/w; and the one or more surfactants are about 5% w/w.

Embodiment 14 relates to the solid dispersion according to any one of Embodiments 8-13, further comprising one or more glidants; one or more disintegrants; one or more filler/binders; and one or more lubricants.

Embodiment 15 relates to the solid dispersion according to Embodiment 14, wherein the one or more glidants range from about 0.5% w/w to about 4% w/w; the one or more disintegrants range from about 3% w/w to about 9% w/w; the one or more filler/binders range from about 20% w/w to about 40% w/w; the one or more lubricants range from about 0.25% w/w to about 1.25% w/w; and wherein the combination of Compound I, HPMCAS and surfactant ranges from about 45.75% w/w to about 76.25% w/w.

Embodiment 16 relates to the solid dispersion according to Embodiment 14, wherein the one or more glidants range from about 1.0% w/w to about 3% w/w; the one or more disintegrants range from about 4% w/w to about 8% w/w; the one or more filler/binders range from about 25% w/w to about 35% w/w; the one or more lubricants range from about 0.5% w/w to about 1.0% w/w; and wherein the combination of Compound I, HPMCAS and surfactant ranges from about 53% w/w to about 69.5% w/w.

Embodiment 17 relates to the solid dispersion according to Embodiment 14, wherein the one or more glidants range from about 1.5% w/w to about 2.5% w/w; the one or more disintegrants range from about 5% w/w to about 7% w/w; the one or more filler/binders range from about 29% w/w to about 33% w/w; the one or more lubricants range from about 0.7% w/w to about 0.8% w/w; and wherein the combination of Compound I, HPMCAS and surfactant ranges from about 56.7% w/w to about 63.8% w/w.

Embodiment 18 relates to the solid dispersion according to any one of Embodiments 14-17, wherein the one or more glidants are selected from the group consisting of colloidal silicon dioxide, finely divided silicon dioxide, silicified microcrystalline cellulose, magnesium oxide, polyethylene glycol and croscarmellose sodium; the one or more disintegrants are selected from the group consisting of sodium bicarbonate, sodium starch glycolate, croscarmellose sodium, and crospovidone; the one or more filler/binders are selected from the group consisting of microcrystalline cellulose, mannitol, sorbitol, maltodextrin, maltose, dextrin, dibasic calcium phosphate dihydrate, dibasic calcium phosphate anhydrate, partially pregelatinized starch, and tribasic calcium phosphate; and the one or more lubricants are selected from the group consisting of magnesium stearate, stearic acid, palmitic acid, calcium stearate, carnauba wax, hydrogenated vegetable oils, mineral oil, polyethylene glycols and sodium stearyl fumarate.

Embodiment 19 relates to the solid dispersion according to any one of Embodiments 14-18, wherein the one or more glidants is colloidal silicon dioxide; the one or more disintegrants is croscarmellose sodium; the one or more filler/binders are mannitol and microcrystalline cellulose, and the one or more lubricants is sodium stearyl fumarate.

Embodiment 20 relates to the solid dispersion according to Embodiment 19, wherein the weight ratio of mannitol to microcrystalline cellulose ranges from about 2:3 to about 3:2.

Embodiment 21 relates to the solid dispersion according to Embodiment 19, wherein the weight ratio of mannitol to microcrystalline cellulose ranges from about 1.1:1.0 to about 1.0:1.1.

Embodiment 22 relates to the solid dispersion according to any one of Embodiments 19-21, wherein the microcrystalline cellulose is selected from the group consisting of Avicel PH-101, Avicel PH-102, Avicel PH-105, Avicel PH-112 and a combination thereof.

Embodiment 23 relates to the solid dispersion according to any one of Embodiments 19-22, wherein microcrystalline cellulose is a combination of Avicel PH-105 and Avicel PH-101.

Embodiment 24 relates to the solid dispersion according to any one of Embodiments 19-23, wherein intragranular microcrystalline cellulose is Avicel PH-105 and extragranular microcrystalline cellulose is Avicel PH-101.

Embodiment 25 relates to the solid dispersion according to Embodiment 24, wherein ratio of Avicel PH-105 and Avicel PH-101 is from about 1:1 to about 1:3.

Embodiment 26 relates to the solid dispersion according to Embodiment 25, wherein ratio of Avicel PH-105 and Avicel PH-101 is from about 1:1.8 to about 1:2.2.

Embodiment 27 relates to the solid dispersion according Embodiment 1, further comprising one or more solubilizing agents.

Embodiment 28 relates to the solid dispersion according to Embodiment 27, wherein the one or more solubilizing agents are selected from the group consisting of sodium taurocholate, Labrasol, poloxamer, polyethylene glycol, copovidone, Transcutol P, propylene glycol, Gelucire 44/14, HCO-60, ethanol, Cremophor EL, Tween 80, 2 hydroxypropyl-beta-cyclodextrin and dimethylsulfoxide.

Embodiment 29 relates to the solid dispersion according to Embodiment 28, wherein the one or more solubilizing agents are poloxamer 407, polyethylene glycol 400, and copovidone.

Embodiment 30 relates to the solid dispersion according to any one of Embodiments 27-29, further comprising one or more glidants; one or more disintegrants; one or more fillers/binders; one or more lubricants; one or more one or more surfactants; and one or more osmogens.

Embodiment 31 relates to the composition of Embodiment 30, wherein Compound I ranges about 5% w/w to about 12% w/w; the one or more solubilizing agents range from about 35% w/w to about 65% w/w; the one or more glidants range from about 0.5% w/w to about 2% w/w; the one or more fillers/binders range from about 8% w/w to about 22% w/w; the one or more surfactants range from about 0.5% w/w to about 4% w/w; the one or more disintegrants range from about 12% w/w to about 24% w/w; the one or more lubricants range from about 0.25% w/w to about 3.0% w/w; and the one or more osmogens range from about 2% w/w to about 6% w/w.

Embodiment 32 relates to the composition of Embodiment 30, wherein Compound I ranges about 7% w/w to about 10% w/w; the one or more solubilizing agents range from about 45% w/w to about 55% w/w; the one or more glidants range from about 0.75% w/w to about 1.5% w/w; the one or more fillers/binders range from about 12% w/w to about 18% w/w; the one or more surfactants range from about 1% w/w to about 3% w/w; the one or more disintegrants range from about 16% w/w to about 20% w/w; the one or more lubricants range from about 0.50% w/w to about 2% w/w; and the one or more osmogens range from about 3% w/w to about 5% w/w.

Embodiment 33 relates to the composition of Embodiment 30, wherein Compound I ranges about 7.5% w/w to about 8.5% w/w; the one or more solubilizing agents range from about 48% w/w to about 52% w/w; the one or more glidants range from about 0.9% w/w to about 1.1% w/w; the one or more fillers/binders range from about 14% w/w to about 16% w/w; the one or more surfactants range from about 1.5% w/w to about 2.5% w/w; the one or more disintegrants range from about 17% w/w to about 19% w/w; the one or more lubricants range from about 0.75% w/w to about 1.25% w/w; and the one or more osmogens range from about 3.5% w/w to about 4.55% w/w.

Embodiment 34 relates to the solid dispersion according to any one of Embodiments 30-33, wherein the one or more surfactants are poloxamer 407, polyethylene glycol 400, and copovidone; the one or more glidants are selected from the group consisting of colloidal silicon dioxide, finely divided silicon dioxide, silicified microcrystalline cellulose, magnesium oxide, polyethylene glycol and croscarmellose sodium; the one or more disintegrants are selected from the group consisting of sodium bicarbonate, sodium starch glycolate, croscarmellose sodium, and crospovidone; the one or more filler/binders are selected from the group consisting of microcrystalline cellulose, mannitol, sorbitol, maltodextrin, maltose, dextrin, dibasic calcium phosphate dihydrate, dibasic calcium phosphate anhydrate, partially pregelatinized starch, and tribasic calcium phosphate; the one or more lubricants are selected from the group consisting of magnesium stearate, stearic acid, palmitic acid, calcium stearate, carnauba wax, hydrogenated vegetable oils, mineral oil, polyethylene glycols and sodium stearyl fumarate; the surfactant is sodium lauryl sulfate; and the osmogen is sodium chloride.

Embodiment 35 relates to the solid dispersion of Embodiment 34, wherein the one or more surfactants are poloxamer 407, polyethylene glycol 400, and copovidone; the one or more glidants is colloidal silicon dioxide; the one or more disintegrants are sodium bicarbonate, croscarmellose sodium, and crospovidone; the one or more filler/binders are microcrystalline cellulose and mannitol; the lubricant is magnesium stearate; the surfactant is sodium lauryl sulfate; and the osmogen is sodium chloride.

Embodiment 36 relates to the solid dispersion according to any one of Embodiments 1-35, wherein the composition is in a tablet form suitable for oral dosage.

Embodiment 36(a) relates to Embodiment 32, wherein the tablet contains 50-500 mg of Compound I.

Embodiment 36(b) relates to Embodiment 32, wherein the tablet contains 75-300 mg of Compound I.

Embodiment 36(c) relates to Embodiment 32, wherein the tablet contains 75-200 mg of Compound I.

Embodiment 36(d) relates to Embodiment 32, wherein the tablet contains 75-150 mg of Compound I.

Embodiment 36(e) relates to Embodiment 32, wherein the tablet contains 75-150 mg of Compound I.

Embodiment 36(f) relates to Embodiment 32, wherein the tablet contains 75-150 mg of Compound I.

Embodiment 37 relates to the solid dispersion according to Embodiment 32, wherein the tablet is suspended in water or a water containing solvent.

Embodiment 37(a) relates to the solid dispersion according to any of the embodiments described herein, wherein the solid dispersion is in a sachet form suitable for oral dosage.

Embodiment 37(b) relates to a tablet comprising the solid dispersion according to any of the embodiments described herein, wherein the tablet contains 150 mg of Compound I.

Embodiment 37(c) relates Embodiment 37(b) wherein the solid dispersion is a spray dry dispersion.

Embodiment 37(d) relates to Embodiment 37(b) or 37(c), wherein the tablet is suspended in an aqueous solution optionally containing a flavoring agent.

Embodiment 37(e) relates to Embodiment 37(d), wherein the tablet is suspended in water optionally containing a flavoring agent. A non-limiting example of a flavoring agent in this embodiment includes crystal light.

Non-limiting examples of glidants that can be used in the solid dispersions of this disclosure include colloidal silicon dioxide, finely divided silicon dioxide, silicified microcrystalline cellulose, magnesium oxide, polyethylene glycol and croscarmellose sodium, and the like, or mixtures thereof. In one aspect, the solid dispersion of this disclosure contains colloidal silicon dioxide as the lubricant. All aforementioned lubricants are commercially available.

Non-limiting examples of fillers/binders that can be used in the solid dispersions of this disclosure include microcrystalline cellulose, mannitol, sorbitol, maltodextrin, maltose, dextrin, dibasic calcium phosphate dihydrate, dibasic calcium phosphate anhydrate, partially pregelatinized starch, and tribasic calcium phosphate, and the like, or mixtures thereof. In certain embodiments, the solid dispersions of this disclosure contain both microcrystalline cellulose and mannitol as fillers/binders. All aforementioned excipients are commercially available.

Non-limiting examples disintegrants that can be used in the solid dispersions of this disclosure include sodium bicarbonate, sodium starch glycolate, croscarmellose sodium, crospovidone, and the like, or mixtures thereof. In other embodiments, solid dispersion of this disclosure contains sodium bicarbonate, croscarmellose sodium, and crospovidone as the disintegrants. In other embodiments, the solid dispersion of this disclosure contains croscarmellose sodium as the disintegrant. All aforementioned disintegrants are commercially available.

Non-limiting examples lubricants that can be used in the solid dispersions of this disclosure include magnesium stearate, stearic acid, palmitic acid, calcium stearate, carnauba wax, hydrogenated vegetable oils, mineral oil, polyethylene glycols, sodium stearyl fumarate, and the like, or mixtures thereof. In one aspect, the lubricant is magnesium stearate or sodium stearyl fumarate. In other embodiments, the solid dispersions of this disclosure contain sodium stearyl fumarate as the lubricant. All aforementioned lubricants are commercially available.

Non-limiting examples or solubilizing agents that can be used in the solid dispersions of this disclosure include sodium taurocholate, Labrasol, poloxamer, polyethylene glycol, copovidone, Transcutol P, propylene glycol, Gelucire 44/14, HCO-60, ethanol, Cremophor EL, Tween 80, 2 hydroxypropyl-beta-cyclodextrin and dimethylsulfoxide. In other embodiments, the solid dispersions of this disclosure contain poloxamer, polyethylene glycol, copovidone as the solubilizing agents. In other embodiments, the solid dispersions of this disclosure contain poloxamer-407, polyethylene glycol 400, and copovidone as the solubilizing agents. All aforementioned solubilizing agents are commercially available.

In another embodiment, the solubilizing agent used in the solid dispersions of this disclosure includes a poloxamer. Poloxamer is available in different grades. Examples of available grades include poloxamer (68, 88, 98, 108, 124, 188, 237, 338, and 407). In another embodiment, the poloxamer is Poloxamer 407. All of the aforementioned poloxamers are commercially available.

In other embodiments of this disclosure, the weight ratio of Compound I to Poloxamer ranges from about 2:3 to about 3:2. In other embodiments of this disclosure, the weight ratio of Compound I to Poloxamer ranges from about 3:4 to about 4:3. In other embodiments of this disclosure, the weight ratio of Compound I to Poloxamer ranges from about 4:5 to about 5:4. In other embodiments of this disclosure, the weight ratio of Compound I to Poloxamer ranges from about 9:10 to about 10:9. In other embodiments of this disclosure, the weight ratio of Compound I to Poloxamer is about 1:1.

In other embodiments of this disclosure, the crospovidone in any of the compositions described herein is Polyplasdone® Ultra, Polyplasdone® Ultra-10, Polyplasdone® XL, or Polyplasdone® XL-10. In other embodiments of this disclosure, the crospovidone in any of the compositions described herein is Polyplasdone® Ultra or Polyplasdone® Ultra-10.

In other embodiments of this disclosure, the solid dispersion of Compound I can be manufactured using an amorphous formulation approach. Other embodiments of this disclosure relate to a solid dispersion manufactured by any of the amorphous formulation approaches described in this disclosure. In certain embodiments, a hot-melt-extrusion (HME) process can be used to formulate amorphous solid dispersion formulations of Compound I. In other embodiments, a spray dry dispersion process can be used to formulate amorphous solid dispersion formulations of Compound I. In other embodiments, the amorphous solid dispersion formulations of Compound I can be capsuled or tableted. In other embodiments, the amorphous solid dispersion formulations of Compound I can be capsuled. In other embodiments, the amorphous solid dispersion formulations of Compound I can be tableted.

Methods of Manufacturing Solid Dispersions of Compound I

Solid Dispersions of Amorphous Compound I Manufactured by Hot Melt Extrusion

Solid Dispersions of amorphous Compound I can be formulated using a hot-melt extrusion process (referred to herein as formulation, HMIE solid dispersion formulation, or HME formulation) comprising hot-melt extrusion, milling, blending, and optionally tableting. Multiple hot-melt extrusion and milling batches may be combined for blending and tableting to make larger batch sizes.

The amounts of materials used for making the solid dispersions are within the weight percentages or ratios ranges in any of the embodiments described in this disclosure.

Hot-Melt Extrusion and Milling

Suitable amounts of Compound I and one or more solubilizing agents, such as copovidone as a non-limiting example, are added to a blender and blended for about 5 minutes. Non-limiting examples of blending/mixing equipment that can be used include a diffusion mixer (for example, V-blender or bin-blender) or a convection mixer (for example, a vertical high intensity mixer). In another embodiment, a V-blender is used for the blending/mixing. The contents are then screen sieved and then transferred back to the blender and blended for about 10 minutes.

A suitable amount of one or more solubilizing agents (such as polyethylene glycol 400 (PEG400)) are weighed in a suitable container. An additional about 20 g of PEG 400 is used for setting up the extruder, and this additional about 20 g of PEG 400 was not part of the solid dispersion. An extruder is set up using appropriate set points and using about 20 g of PEG 400 to adjust the flow rate.

The blend is added to a feed hopper and the extrusion process is initiated. The extrusion parameters are adjusted and monitored as necessary. The resulting pelletized extrusion are collected and can be weighed and placed in a suitable container.

Blending

To the milled extrudate are added the following materials in the amounts described in this disclosure. The following excipients are first weighed and screen/milled prior to adding them to the milled extrudate: One or more glidants, such as colloidal silicon dioxide as a non-limiting example; one or more disintegrants, such as croscarmellose sodium, crospovidone, and sodium bicarbonate as a non-limiting example; one or more fillers/binders, such as mannitol and microcrystalline cellulose as a non-limiting example; one or more solubilizing agents, such as poloxamer 407 as a non-limiting example; one or more osmogens, such as sodium chloride as a non-limiting example; and one or more surfactants, such as sodium lauryl sulfate as a non-limiting example. The milled extrudate and the screened excipients are added to blender, such as a bin-blender for example, and blended.

To the blender is then added a lubricant, such as magnesium stearate, which is then blended. The lubricant can be weighed out and screened prior to the addition to the blender.

The blend can then be tableted by transferring the blend to a rotary tablet press hopper for tableting. A tablet press can be set up to yield target tablet weight, hardness, and friability. The tableted blend can be monitored for tablet weight and hardness.

Solid Dispersions of Amorphous Compound I Manufactured by Spray Dry Dispersion

The amounts of materials used for making the solid dispersions are within the weight percentages or ratio ranges in any of the embodiments described in this disclosure.

Spray solution solvents, such as acetone and water as non-limiting examples; HPMCAS; one or more surfactants; and Compound I are weighed and put into a suitable container. The surfactant is slowly added into the spray solution of Step 1 while mixing, followed by Compound I, and mixing is continued. During mixing, the HPMCAS is slowly added and mixing is continued. The resulting solution is spray dried using a standard pharmaceutical grade spray dryer, such as MS-150. Following completion of spray drying, the Spray-Dried Dispersion (SDD) is dried in an oven until the residual acetone is below ICH guidelines, 5000 ppm. The dried SDD is then transferred into appropriate containers with desiccants to protect from moisture. This SDD has been tested to have pharmacological activity as demonstrated in dogs within disclosure. This SDD can be further formulated by dry granulation and blending as described below.

Dry Granulation and Blending of Spray Dry Dispersion with Intragranular and Extragranular Excipients The dried SDD and intra-granular excipients can be dispensed into appropriate containers. The intra-granular excipients employed are one or more lubricants (such as sodium stearyl fumarate as a non-limiting example); one or more glidants (such as colloidal silicon dioxide as a non-limiting example); one or more disintegrants (such as croscarmellose sodium as a non-limiting example); and one or more fillers/binders (such as mannitol and microcrystalline cellulose as non-limiting examples). The SDD and intra-granular excipients are added to a blender of an appropriate size and blended. The blend is passed through a sieve (such as a comil) to improve blend uniformity and remove large particles. This blend is further blended and then discharged into appropriate container.

The blend is then dry granulated to result in ribbons using an appropriate roller compactor, such as TFC-220 roller compactor or others, and by using selected process parameters (roll type, RPM and roll compaction force). The resulting ribbons are milled (which can be done by using a comil, for example) to result in a free flowing granulation.

Appropriate quantities of the extra-granular excipients are then added. The extra granular excipients include one or more lubricants (such as sodium stearyl fumarate as a non-limiting example); one or more glidants (such as colloidal silicon dioxide, and croscarmellose sodium as a non-limiting example); to the granulation and blend to obtain the blend for tablet compression.

The granulated SDD can then be tableted and packaged as described below.

Tableting

The granulated SDD can be tableted with a rotary tablet press. The rotary tablet press is set up to yield target tablet weight, hardness, and friability. Weight and hardness can be monitored at initial startup and at about 15 minute intervals. Metal check and weight sorting can be performed for the tablets.

In one embodiment, the method of preparing the composition of this disclosure comprises mixing Compound I, or a pharmaceutically acceptable salt thereof, and a solubilizing agent. Non-limiting examples of mixing equipment that can be used in preparing the compositions of this disclosure include a diffusion mixer (for example, V-blender or bin-blender) or a convection mixer (for example, a vertical high intensity mixer). Another embodiment of this disclosure relates to a composition prepared by this method.

In other embodiments, the composition of this disclosure comprises solid dispersions of Compound I and a carrier. As used herein, the term "carrier" is meant to include liposomes and nanoparticles (such as naturally-equipped nanocarriers, for example, exosomes), and the like. It is known that exosomes can be highly effective drug carriers, and there are various ways in which drugs can be loaded into exosomes, including those techniques described in J Control Release, 2015 Dec. 10; 219: 396-405, the contents of which are incorporated by reference in its entirety.

Methods of Treatment

In some embodiments, the disclosure provides a method for treating a disease or condition in a subject in need thereof, by administering to the subject a therapeutically effective amount of any of the solid dispersions of Compound I described herein.

In some embodiments, the disclosure provides a method of treating a subject with a BRAF mutation related disease or condition comprising administering a solid dispersion of Compound I of this disclosure. In other embodiments, the BRAF mutation related disease or condition is a BRAF V600 mutation related disease or condition. Non limiting examples of BRAF V600 mutations include V600E, V600K, V600A, V600G, V600M, and V600R. In other embodiments, the BRAF mutation related disease or condition is a BRAF V600Emutation related disease or condition.

The BRAF V600E mutation occurs in about half of all melanomas (Rajagopalan 2002) and in many additional cancers, as well as other types of disease or conditions. The following BRAF V600E mutation related diseases or conditions are contemplated for the methods and uses of Compound I described herein.

Non-limiting examples of BRAF V600 mutation related diseases or conditions include melanoma (including metastatic melanoma, stage 3A melanoma, stage 3B melanoma, stage 3C melanoma, and skin pigmentation melanoma), colorectal cancer (including colorectal adenocarcinoma) (Cohen 2003), papillary thyroid cancer (Fukushima 2003; Kimura 2003; Xu 2003), anaplastic thyroid cancer (Xu 2003), serous ovarian cancer (Nikiforova 2003), non-small-cell lung cancer (Singer 2003), gastric cancer (Brose 2002), cholangiocarcinoma (Lee 2003), Barrett's esophageal cancer (Tannapfel 2003), and head and neck cancers (Sommerer 2004; Weber 2003). Other non-limiting examples of BRAF V600 mutation related cancers include hepatocellular carcinoma (Colombino 2012), Langerhan's cell histiocytosis (Badalian-Very 2010), gastrointestinal stromal cell tumors (Agaram 2008), multiple myeloma (Chapman 2011), pediatric astrocytomas (which contain mostly BRAF duplications) (Jones 2008; Pfister 2008; Sievert 2009), pleomorphic xanthoastrocytomas (Dias-Santagata 2011; Schindler 2011), chronic myeloid leukemia, acute myelomonocytic leukemia, biphenotypic B myelomonocytic leukemia, acute myeloid leukemia, and hairy cell leukemia (Tiacci 2011). Other non-limiting examples of BRAF V600 mutation related cancer include peripheral nerve sheath tumors, such as benign and malignant peripheral nerve sheath tumors (Serrano 2013). BRAF V600 mutations are also very frequent in nevi (Pollock 2003), which are generally dysplastic lesions that derive from melanocytes and are quiescent and thus benign. BRAF V600 mutations also occurs in Erdheim-Chester disease.

Other BRAF 600V related conditions or disorders include inflammatory and autoimmune disease (such as rheumatoid arthritis) (Mol Immunol. 2013 October; 55(3-4):247-52), tenosynovial giant cell tumor, pigmented villonodular synovitis, giant cell tumor of tendon sheath, giant cell tumor of bone, cervical cancer (Gynecol Oncol. 2007 June; 105(3): 662-6.), endometrial cancer (Fam Cancer. 2014 March; 13(1):1-12), germ cell tumors (J Clin Oncol. 2009 May 1; 27(13):2129-36), prostate cancer (Genes Chromosomes Cancer. 2012 November; 51(11):1014-23), bladder cancer (Mol Cancer Res. 2015 Mar. 12. pii: molcanres.0689.2014), myopericytoma (J Natl Cancer Inst. 2014 Jul. 25; 106(8)), metanephric adenoma (Am J Surg Pathol. 2015 April; 39(4): 549-57), pancreatic neoplasms (J Pathol. 2014 March; 232 (4):428-35), neuroendocrine tumors (Am J Clin Pathol. 2005 February; 123(2):256-60), endocrine tumors (Endocr Relat Cancer. 2004 December; 11(4):855-60), adrenal tumors (Endocr Relat Cancer. 2009 June; 16(2):565-72), adrenal medullary tumors, cystadenocarcinoma of the parotid (Springerplus. 2013 Dec. 18; 2:679. doi: 10.1186/2193-1801-2-679), glioblastoma multiforme (World J Surg Oncol. 2015 Mar. 11; 13:100), bile duct cancer including bile duct adenoma (Hepatology. 2015 January; 61(1):403-5), choloangiocarcinoma, B-cell chronic lymphoproliferative disorder (Blood. 2012 Jan. 5; 119(1):188-91), dendritic cell sarcomas (Ann Diagn Pathol. 2015 June; 19(3):113-6), histiocytic sarcomas, and lymphoma (e.g. Richter's syndrome, non-Hodgkin's lymphoma) (Cell. 2015 Apr. 9; 161 (2):319-32).

Embodiment 38 of this disclosure relates to a method of treating a BRAF mutation related disease or condition, comprising administering to a subject in need thereof a therapeutically effective amount of a solid dispersion according to any Embodiments 1-37, including any sub-embodiments thereof described herein, wherein the BRAF mutation related disease or condition is melanoma, colorectal cancer, papillary thyroid cancer, papillary craniopharyngiomas, anaplastic thyroid cancer, ovarian cancer, non-small-cell lung cancer, gastric cancer, cholangiocarcinoma, Barrett's esophageal cancer, head and neck cancer, hepatocellular carcinoma, breast cancer, Langerhan's cell histiocytosis, gastrointestinal stromal cell tumors (GIST), multiple myeloma, pediatric astrocytomas, pleomorphic xanthoastrocytomas, chronic myeloid leukemia, acute myelomonocytic leukemia, biphenotypic B myelomonocytic leukemia, acute myeloid leukemia, hairy cell leukemia, nevi, Erdheim-Chester Disease, malignant peripheral nerve sheath tumor, inflammatory and autoimmune disease, tenosynovial giant cell tumor, pigmented villonodular synovitis, giant cell tumor of tendon sheath, giant cell tumor of bone, cervical cancer, endometrial cancer, germ cell tumors, prostate cancer, bladder cancer, myopericytoma, metanephric adenoma, pancreatic neoplasms, neuroendocrine tumors, endocrine tumors, adrenal tumors, adrenal medullary tumors, cystadenocarcinoma of the parotid, glioblastoma multiforme, bile duct cancer including bile duct adenoma, B-cell chronic lymphoproliferative disorder, dendritic cell sarcomas, histiocytic sarcomas, or lymphoma.

Embodiment 38(a) of this disclosure relates to Embodiment 38, wherein the BRAF mutation related disease or condition is Erdheim-Chester disease.

Embodiment 38(b) of this disclosure relates to Embodiment 38, wherein the BRAF mutation related disease or condition is melanoma.

Embodiment 38(c) of this disclosure relates to Embodiment 38, wherein the BRAF mutation related disease or condition is metastatic melanoma.

Embodiment 38(d) of this disclosure relates to Embodiment 38, wherein the BRAF mutation related disease or condition is colorectal cancer.

Embodiment 38(e) of this disclosure relates to Embodiment 38, wherein the BRAF mutation related disease or condition is papillary thyroid cancer.

Embodiment 38(f) of this disclosure relates to Embodiment 38, wherein the BRAF mutation related disease or condition is papillary craniopharyngiomas.

Embodiment 38(g) of this disclosure relates to Embodiment 38, wherein the BRAF mutation related disease or condition is Ovarian Cancer.

Embodiment 38(h) of this disclosure relates to Embodiment 38, wherein the BRAF mutation related disease or condition is anaplastic thyroid cancer.

Embodiment 38(i) of this disclosure relates to Embodiment 38, wherein the BRAF mutation related disease or condition is non-small-cell lung cancer.

Embodiment 38(j) of this disclosure relates to Embodiment 38, wherein the BRAF mutation related disease or condition is gastric cancer.

Embodiment 38(k) of this disclosure relates to Embodiment 38, wherein the BRAF mutation related disease or condition is Langerhan's cell histiocytosis.

Embodiment 38(l) of this disclosure relates to Embodiment 38, wherein the BRAF mutation related disease or condition is pediatric astrocytomas.

Embodiment 38(m) of this disclosure relates to Embodiment 38, wherein the BRAF mutation related disease or condition is glioblastoma.

Embodiment 38(n) of this disclosure relates to Embodiment 38, wherein the BRAF mutation related disease or condition is multiple myeloma.

Embodiment 38(o) of this disclosure relates to Embodiment 38, wherein the BRAF mutation related disease or condition is prostate cancer.

Embodiment 38(p) of this disclosure relates to Embodiment 38, wherein the BRAF mutation related disease or condition is bladder cancer.

Embodiment 38(q) of this disclosure relates to Embodiment 38, wherein the BRAF mutation related disease or condition is GIST, gastric cancer or Barrett's esophageal cancer.

Embodiment 38(r) of this disclosure relates to Embodiment 38, wherein the BRAF mutation related disease or condition is Head and Neck cancer.

Embodiment 39 of this disclosure relates to a method according to Embodiment 38, wherein the BRAF mutation related disease or condition is hepatocellular carcinoma, Langerhan's cell histiocytosis, Erdheim Chester Disease, gastrointestinal stromal cell tumors, hairy cell leukemia, hairy cell leukemia, melanoma, colorectal cancer, papillary thyroid cancer, anaplastic thyroid cancer, ovarian cancer, non-small-cell lung cancer, colorectal cancer, glioblastoma multiforme, prostate cancer, gastric cancer, cholangiocarcinoma, or Barrett's esophageal cancer.

Combination Therapies

In some embodiments, the disclosure provides methods of treating any of the diseases or conditions described herein in an animal subject in need thereof, wherein the method involves administering to the subject an effective amount of the solid dispersions of Compound I of this disclosure in combination with one or more other therapies for the disease or condition.

A. Compound I in Combination with Another Agent

In another aspect, the disclosure provides a method for treating a cancer in a subject in need thereof by administering to the subject an effective amount of the solid dispersions of Compound I of this disclosure with one or more suitable chemotherapeutic agents. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosfamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy including indoleamine 2,3-dioxygenase (IDO) inhibitors, an antibody therapy, including, but not limited to immune checkpoint inhibitors such as PD-1 inhibitors (such as pembrolizumab, nivolumab, pidilizumab) or PD-L1 inhibitors (such as BMS-936559, MEDI4736, MPDL3280A, or MSB0010718C), alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, cabozantinib, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, and vatalanib; a targeted signal transduction inhibitor including, but not limited to bortezomib, geldanamycin, and rapamycin; a biological response modifier, including, but not limited to, imiquimod, interferon-γ, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. INK28, AZD8055, sirolimus, temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib), and Aromatase inhibitors (anastrozole letrozole exemestane). In another embodiment of the methods and uses described herein, solid dispersions described herein are administered in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin 2, or erlotinib. In another embodiment, the chemotherapeutic agent is a Mek inhibitor. Exemplary Mek inhibitors include, but are not limited to trametinib, cobimetinib, AS703026, AZD6244 (Selumetinib), AZD8330, BIX 02188, CI-1040 (PD184352), GSK1120212 (JTP-74057), PD0325901, PD318088, PD98059, RDEA119(BAY 869766), TAK-733 and U0126-EtOH. In another embodiment, the chemotherapeutic agent is a tyrosine kinase inhibitor. Exemplary tyrosine kinase inhibitors include, but are not limited to, AEE788, AG-1478 (Tyrphostin AG-1478), AG-490, Apatinib (YN968D1), AV-412, AV-951(Tivozanib), Axitinib, AZD8931, BIBF1120 (Vargatef), BIBW2992 (Afatinib), BMS794833, BMS-599626, Brivanib (BMS-540215), Brivanib alaninate (BMS-582664), Cediranib (AZD2171), Chrysophanic acid (Chrysophanol), Crenolanib (CP-868569), CUDC-101, CYC116, Dovitinib Dilactic acid (TKI258 Dilactic acid), E7080, Erlotinib Hydrochloride (Tarceva, CP-358774, OSI-774, NSC-718781), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib(TAK 165), Neratinib (HKI-272), NVP-BHG712, OSI-420 (Desmethyl Erlotinib, CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, Cabozantinib, XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), and DPP4 inhibitors (sitagliptin, vildagliptin, saxagliptin, dutogliptin, gemigliptin, alogliptin). In another embodiment, the agent is a BET inhibitor (such as BRD2, BRD3, BRD4 and/or BRDT). In another embodiment, the agent is an EGFR inhibitor. Exemplary EGFR inhibitors include, but are not limited to, AEE-788, AP-26113, BIBW-2992 (Tovok), CI-1033, GW-572016, Iressa, LY2874455, RO-5323441, Tarceva (Erlotinib, OSI-774), CUDC-101, cetuximab and WZ4002. In another embodiment, the disclosure provides a method for treating a cancer in a subject in need thereof by administering to the subject an effective amount of the solid dispersion described herein with a topoisomerase inhibitor (such as irinotecan) and an EGFR inhibitor (such as cetuximab). In another embodiment, the disclosure provides a method for treating a cancer in a subject in need thereof by administering to the subject an effective amount of the solid dispersion described herein with a G-protein coupled estrogen receptor (GPER) agonist.

In other embodiments, the methods of treating BRAF mutant related diseases or conditions of this disclosure further comprises co-administered with a CYP inhibitor to improve exposure and efficacy of Compound I in the subject being treated.

Embodiment 40 of this disclosure relates to a method according to any one of Embodiments 38, 38(a)-34(r) and 39, further comprising co-administering to said subject a CYP inhibitor.

Embodiment 40(a) of this disclosure relates Embodiment 36 wherein the solid dispersion and the CYP inhibitor are administered sequentially.

Embodiment 41 of this disclosure relates to a method according to Embodiment 36, wherein the CYP inhibitor is CYP3A inhibitor.

Embodiment 42 of this disclosure relates to a method according to Embodiment 41, wherein the CYP3A inhibitor is boceprevir, cobicistat, conivaptan, danoprevir, ritonavir, elvitegravir, ritonavir, grapefruit juice, indinavir, ritonavir, itraconazole, ketoconazole, lopinavir, ritonavir, paritaprevir, ritonavir, ombitasvir, dasabuvir, posaconazole, ritonavir, saquinavir, ritonavir, telaprevir, tipranavir, ritonavir, troleandomycin, voriconazole, clarithromycin, diltiazem, idelalisib, nefazodone, nelfinavir, or a combination thereof.

Embodiment 42 (a) of this disclosure relates to a method according to Embodiment 41, wherein the CYP3A inhibitor is boceprevir, cobicistat, conivaptan, danoprevir and ritonavir, elvitegravir and ritonavir, grapefruit juice, indinavir and ritonavir, itraconazole, ketoconazole, lopinavir and ritonavir, posaconazole, ritonavir, saquinavir and ritonavir, telaprevir, tipranavir and ritonavir, troleandomycin, voriconazole, clarithromycin, diltiazem, idelalisib, nefazodone, nelfinavir, or paritaprevir and ritonavir and ombitasvir and/or dasabuvir.

Embodiment 43 of this disclosure relates to a method according to Embodiment 42, wherein the CYP3A inhibitor is cobicistat.

B. Solid Dispersion of Compound I in Combination with Another Therapy

In some embodiments, the disclosure provides a method of treating a cancer in a subject in need thereof by administering to the subject an effective amount of the solid dispersions of Compound I in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, y-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), oncolytic viral or bacterial therapy, surgery, or bone marrow and stem cell transplantation. In certain embodiments, the disclosure provides a method of treating a cancer in a subject in need thereof by administering to the subject an effective amount of a compound of a solid dispersion of Compound I described herein and applying a radiation treatment as described herein either separately or simultaneously. In one embodiment, the disclosure provides a method for treating a cancer in a subject in need thereof by administering an effective amount of a solid dispersion of Compound I described herein to the subject followed by a radiation treatment (e.g. x-ray, y-ray, or electron, proton, neutron, or a particle beam). In another embodiment, the disclosure provides a method for treating a cancer in a subject in need thereof by applying a radiation treatment (e.g. x-ray, y-ray, or electron, proton, neutron, or a particle beam) to the subject followed by administering an effective amount of a solid dispersion of Compound I described herein to the subject. In yet another embodiment, the disclosure provides a method for treating a cancer in a subject in need thereof by administering a solid dispersion of Compound I described herein and a radiation therapy (e.g. x-ray, y-ray, or electron, proton, neutron, or a particle beam) to the subject simultaneously.

Kinase Activity Assays

A number of different assays for kinase activity can be utilized for assaying for active modulators and/or determining specificity of a modulator for a particular kinase or group of kinases, such as those described in U.S. Pat. Pub. No. Publication US 2016/0339025 A1, which is hereby incorporated by reference in its entirety. One of ordinary skill in the art can readily identify other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Abbreviations as used herein have respective meanings as follows:

| | |
|---|---|
| AUC | Area under the curve |
| brs | Broad singlet |
| d | Doublet |
| DMSO | Dimethylsulfoxide |
| EtOH | Ethanol |
| HPLC | High pressure liquid chromatography |
| Hz | Hertz |
| LCMS | Liquid chromatography mass spectroscopy |
| MHz | Megahertz |
| m | Multiplet |
| ms | Mass spectroscopy |
| NMR | Nuclear magnetic resonance |
| s | Singlet |
| µL | Microliter |
| µm | Micrometer |
| µM | Micromolar |
| w/w | Weight to Weight |

REFERENCES

Agaram, N. P. et al. Novel V600E BRAF mutations in imatinib-naive and imatinib-resistant gastrointestinal stromal tumors. *Genes Chromosomes Cancer* 47, 853-859 (2008).

Anforth R M, Blumetti T C M P, Kefford R F, Sharma R, Scolyer R a, Kossard S, et al. Cutaneous manifestations of dabrafenib (GSK2118436): a selective inhibitor of mutant BRAF in patients with metastatic melanoma. Br. J. Dermatol. 2012 November; 167(5):1153-1160.

Badalian-Very, G. et al. Recurrent BRAF mutations in Langerhans cell histiocytosis. *Blood* 116, 1919-1923 (2010).

Bollag G, Hirth P, Tsai J, Zhang J, Ibrahim P N, Cho H, et al. Clinical efficacy of a RAF inhibitor needs broad target blockade in BRAF-mutant melanoma. Nature, 2010 Sep. 30; 467(7315):596-599.

Brose, M. S. et al. BRAF and RAS mutations in human lung cancer and melanoma. *Cancer Res.* 62, 6997-7000(2002).

Callahan M K, Rampal R, Harding J J, Klimek V M, Chung Y R, Merghoub T, et al. Progression of RAS-mutant leukemia during RAF inhibitor treatment. N. Engl. J. Med. 2012 Dec. 13; 367(24):2316-2321.

Chapman, M. A. et al. Initial genome sequencing and analysis of multiple myeloma. *Nature* 471, 467-472 (2011).

Chapman P B, Hauschild A, Robert C, Haanen J B, Ascierto P, Larkin J, et al. for BRIM-3 Study Group. Improved survival with vemurafenib in melanoma with BRAF V600E mutation. N Engl J Med. 2011 Jun. 30; 364(26): 2507-2516.

Cohen, Y. et al. BRAF mutation in papillary thyroid carcinoma. *J. Nat Cancer Inst.* 95, 625-627 (2003).

Colombino, M. et al. BRAF and PIK3C A genes are somatically mutated in hepatocellular carcinoma among patients from South Italy. *Cell Death Dis.* 3, e259 (2012).

Corcoran R B, Ebi H, Turke A B, Coffee E M, Nishino M, Cogdill A P, et al. EGFR-mediated re-activation of MAPK signaling contributes to insensitivity of BRAF mutant colorectal cancers to RAF inhibition with vemurafenib. Cancer Discov. 2012 March; 2(3):227-235.

Davies H, Bignell G R, Cox C, Stephens P, Edkins S, Clegg S, et al. Mutations of the BRAF gene in human cancer. *Nature.* 2002 Jun. 27; 417(6892):949-954.

Dias-Santagata, D. et al. BRAF V600E mutations are common in pleomorphic xanthoastrocytoma: diagnostic and therapeutic implications. *PLoS ONE* 6, e17948 (2011).

Flaherty K T, Puzanov I, Kim K B, Ribas A, McArthur G A, Sosman J A, et al. Inhibition of mutated, activated BRAF in metastatic melanoma. N. Engl. J. Med. 2010 Aug. 26; 363(9):809-819.

Fukushima, T. et al. BRAF mutations in papillary carcinomas of the thyroid. Oncogene 22, 6455-6457(2003).

Hatzivassiliou G, Song K, Yen I, Brandhuber B J, Anderson D J, Alvarado R, et al. RAF inhibitors prime wild-type RAF to activate the MAPK pathway and enhance growth. Nature. Nature Publishing Group; 2010 Mar. 18; 464 (7287):431-435.

Hauschild A, Grob J-J, Demidov L V, Jouary T, Gutzmer R, Millward M, et al. Dabrafenib in BRAF-mutated metastatic melanoma: a multicentre, open-label, phase 3 randomised controlled trial. Lancet. Elsevier Ltd; 2012 Jul. 28; 380(9839):358-365.

Heidorn S J, Milagre C, Whittaker S, Nourry A, Niculescu-Duvas I, Dhomen N, et al. Kinase-dead BRAF and oncogenic RAS cooperate to drive tumor progression through CRAF. Cell. Elsevier Ltd; 2010 Jan. 22; 140(2): 209-221.

Huang V, Hepper D, Anadkat M, Cornelius L. Cutaneous toxic effects associated with vemurafenib and inhibition of the BRAF pathway. Arch. Dermatol. 2012 May; 148 (5):628-633.

Jones, D. T. et al. Tandem duplication producing a novel oncogenic BRAF fusion gene defines the majority of pilocytic astrocytomas. *Cancer Res.* 68, 8673-8677 (2008).

Kimura, E. T. et al. High prevalence of BRAF mutations in thyroid cancer: genetic evidence for constitutive activation of the RET/PTC-RAS-BRAF signaling pathway in papillary thyroid carcinoma. *Cancer Res.* 63, 1454-1457 (2003).

Lacouture M E, Desai a, Soltani K, Petronic-Rosic V, Laumann a E, Ratain M J, et al. Inflammation of actinic keratoses subsequent to therapy with sorafenib, a multi-targeted tyrosine-kinase inhibitor. Clin. Exp. Dermatol. 2006 November; 31(6):783-785.

Lee, S. H. et al. BRAF and KRAS mutations in stomach cancer. *Oncogene* 22, 6942-6945 (2003).

Nazarian R, Shi H, Wang Q, Kong X, Koya R C, Lee H, et al. Melanomas acquire resistance to B-RAF(V600E) inhibition by RTK or N-RAS upregulation. Nature. 2010 Dec. 16; 468(7326):973-977.

Nikiforova, M. N. et al. BRAF mutations in thyroid tumors are restricted to papillary carcinomas and anaplastic or poorly differentiated carcinomas arising from papillary carcinomas. *J. Cin. Endocrinol. Metab.* 88, 5399-5404 (2003).

Oberholzer P a, Kee D, Dziunycz P, Sucker A, Kamsukom N, Jones R, et al. RAS mutations are associated with the development of cutaneous squamous cell tumors in patients treated with RAF inhibitors. J. Clin. Oncol. 2012 Jan. 20; 30(3):316-321.

Pfister, S. et al. BRAF gene duplication constitutes a mechanism of MAPK pathway activation in low-grade astrocytomas. *J. Cin. Invest.* 118, 1739-1749 (2008).

Pollock, P. M. et al. High frequency of BRAF mutations in nevi. Nature Genet. 33, 19-20 (2003).

Poulikakos P I, Persaud Y, Janakiraman M, Kong X, Ng C, Moriceau G, et al. RAF inhibitor resistance is mediated by dimerization of aberrantly spliced BRAF(V600E). Nature. Nature Publishing Group; 2011 Dec. 15; 480(7377):387-390.

Poulikakos P I, Zhang C, Bollag G, Shokat K M, Rosen N. RAF inhibitors transactivate RAF dimers and ERK signalling in cells with wild-type BRAF. Nature. Nature Publishing Group; 2010 Mar. 18; 464(7287):427-430.

Prahallad A, Sun C, Huang S, Di Nicolantonio F, Salazar R, Zecchin D, et al. Unresponsiveness of colon cancer to BRAF(V600E) inhibition through feedback activation of EGFR. Nature. 2012 Mar. 1; 483(7387):100-103.

Rajagopalan, H. et al. Tumorigenesis: RAF/RAS oncogenes and mismatch-repair status. *Nature* 418, 934 (2002).

Robert C, Arnault J-P, Mateus C. RAF inhibition and induction of cutaneous squamous cell carcinoma. Curr. Opin. Oncol. 2011 March; 23(2):177-182.

Schindler, G. et al. Analysis of BRAF V600E mutation in 1,320 nervous system tumors reveals high mutation frequencies in pleomorphic xanthoastrocytoma, ganglioglioma and extra-cerebellar pilocytic astrocytoma. *Acta Neuropathol.* 121, 397-405 (2011).

Serrano C, et al. BRAF V600E and KRAS G12S mutations in peripheral nerve sheath tumours. *Histopathology,* 2013 February; 62(3):499-504.

Sievert, A. J. et al. Duplication of 7q34 in pediatric low-grade astrocytomas detected by high-density single-nucleotide polymorphism-based genotype arrays results in a novel BRAF fusion gene. Brain Pathol. 19, 449-458 (2009).

Singer, G. et al. Mutations in BRAF and KRAS characterize the development of low-grade ovarian serous carcinoma. J. Natl Cancer Inst. 95, 484-486 (2003).

Sommerer, F. et al. Mutations of BRAF and KRAS2 in the development of Barrett's adenocarcinoma. Oncogene 23, 554-558 (2004).

Sosman J A, Kim K B, Schuchter L, Gonzalez R, Pavlick A C, Weber J S, et al. Survival in BRAF V600-mutant advanced melanoma treated with vemurafenib. N. Engl. J. Med. 2012 Feb. 23; 366(8):707-714.

Stellwagen J C, Adjabeng G M, Arnone M R, Dickerson S H, Han C, Hornberger K R, et al. Development of potent B-RafV600E inhibitors containing an arylsulfonamide headgroup. Bioorg. Med. Chem. Lett. Elsevier Ltd; 2011 Aug. 1; 21(15):4436-4440.

Straussman R, Morikawa T, Shee K, Barzily-Rokni M, Qian Z R, Du J, et al. Tumour micro-environment elicits innate resistance to RAF inhibitors through HGF secretion. Nature. 2012 487:500-504.

Su, F., Viros, A., Milagre, C., Trunzer, K., Bollag, G., Spleiss, O., Reis-Filho, J. S., et al. (2012). RAS mutations in cutaneous squamous-cell carcinomas in patients treated with BRAF inhibitors. The New England journal of medicine, 366(3), 207-15.

Tannapfel, A. et al. Mutations of the BRAF gene in cholangiocarcinoma but not in hepatocellular carcinoma. Gut 52, 706-712 (2003).

Tiacci, E. et al. BRAF mutations in hairy-cell leukemia. *N. Engl. J. Med.* 364, 2305-2315 (2011).

Tsai, J., Lee, J. T., Wang, W., Zhang, J., Cho, H., Mamo, S., Bremer, R., et al. (2008). Discovery of a selective inhibitor of oncogenic B-Raf kinase with potent antimelanoma activity. Proceedings of the National Academy of Sciences of the United States of America, 105(8), 3041-6.

Villanueva J, Vultur A, Lee J T, Somasundaram R, Fukunaga-Kalabis M, Cipolla A K, et al. Acquired resistance to BRAF inhibitors mediated by a RAF kinase switch in melanoma can be overcome by cotargeting MEK and IGF-1R/PI3K. Cancer Cell. Elsevier Inc.; 2010 Dec. 14; 18(6):683-695.

Weber, A. et al. Mutations of the BRAF gene in squamous cell carcinoma of the head and neck. *Oncogene* 22, 4757-4759 (2003).

Xu, X., Quiros, R. M., Gattuso, P., Ain, K. B. & Prinz, R. A. High prevalence of BRAF gene mutation in papillary thyroid carcinomas and thyroid tumor cell lines. *Cancer Res.* 63, 4561-4567 (2003).

Zimmer L, Hillen U, Livingstone E, Lacouture M E, Busam K, Carvajal R D, et al. Atypical melanocytic proliferations and new primary melanomas in patients with advanced melanoma undergoing selective BRAF inhibition. J Clin Oncol. 2012 30:2375-2383.

EXAMPLES

Examples related to the present disclosure are described below. In most cases, alternative techniques can be used. The examples are intended to be illustrative and are not limiting or restrictive to the scope of the disclosure.

Example 1: Synthesis of Compound I

Those skilled in the art will also recognize that during standard work up procedures in organic chemistry, acids and bases are frequently used. Salts of the parent compounds are sometimes produced, if they possess the necessary intrinsic acidity or basicity, during the experimental procedures Step 1. Preparation of (5-bromo-1H-pyrrolo[2,3-b]pyridin-3-yl)-(2,6-difluoro-3-nitro-phenyl)methanone (3)

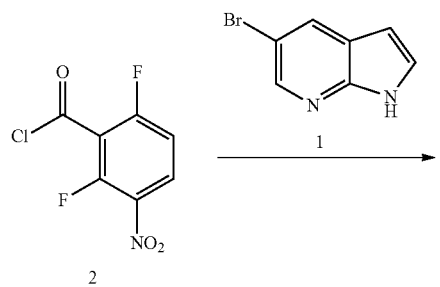

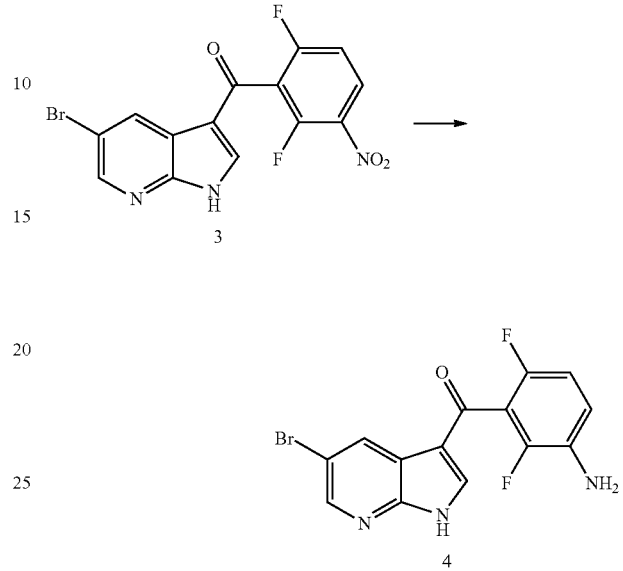

Step 2. Preparation of (3-amino-2,6-difluoro-phenyl)-(5-bromo-1H-pyrrolo[2,3-b]pyridin-3-yl)methanone (4)

To a 50-liter flask was added 1,2-dichloroethane (DCE, 20 L), followed by 5-bromoazaindole (1) (2 kg, 10.152 mol) to result in an orange slurry. Aluminum Chloride (5.421 kg, 40.608 mol) was slowly added to the flask. The first 1.5 kg of the addition was exothermic resulting in a dark solution. The rest of the AlCl₃ was added to give a reaction mixture. To the reaction mixture was added 2,6-difluoro-3-nitrobenzoyl chloride 2 (2.25 kg, 10.125 mol) via an addition funnel over a period of 1.5 h. During the addition, the reaction temperature was maintained at or below 45° C. After the addition, the reaction mixture was stirred at 50° C. overnight, cooled to room temperature (about 22° C.) and transferred into two separate 20 L flasks. Water (25 L) and acetonitrile (12 L) were added to a 50-liter flask and cooled to 0° C. The reaction mixture was quenched by adding water/acetonitrile solution while keeping the temperature at or below 40° C. The mixture obtained was filtered, and the filtrate was washed with acetonitrile:water (1:1, 2×4 L), water (4 L) and acetonitrile (4 L), followed by drying in vacuum. Compound 3 was obtained. MS (ESI): M+H⁺=383.9. ¹H NMR (DMSO-d₆, δ ppm): 7.55 (1H, m), 8.47 (2H, m), 8.53 (1H, d, J=2.2 Hz), 8.65 (1H, d, J=2.2 Hz), 13.25 (1H, s).

A 50-liter flask was added 2-methyl-tetrahydrofuran (2-methyl-THF) (36 L), compound 3 (2.85 kg, 7.455 mol) and tin(II) chloride (5.03 kg, 22.365 mol). The mixture was heated to 60° C. Upon completion, the reaction was quenched with an aqueous potassium carbonate solution (20%). The resulting mixture was filtered with celite and the solid residue was washed with 2-methyl-THF and tetrahydrofuran (THF). The filtrate was washed with an aqueous NaCl solution (15 L, 10%) and the organic layer was separated. The organic layer was further washed with an aqueous NaCl solution (15 L, 20%) and concentrated on a rotovap to yield compound 4. MS (ESI): M+H⁺=353 and 354. ¹H NMR (DMSO-d₆, δ ppm): 5.22 (2H, s), 6.93 (2H, m), 8.12 (1H, s), 8.47 (1H, d J=2.3 Hz), 8.54 (1H, d J–1.6 Hz), 13.2 (1H, s).

Step 3: Preparation of (3-amino-2,6-difluoro-phenyl)-[5-bromo-1-(2,6-dichlorobenzoyl)pyrrolo[2,3-b]pyridin-3-yl]methanone(5)

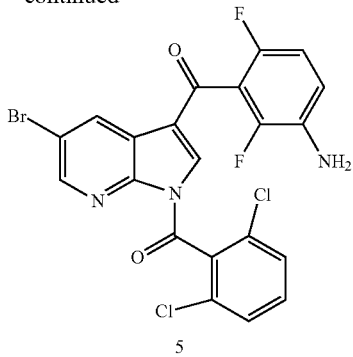

5

Compound 4 (2.5 kg, 7.114 mol) obtained from Step 2 was added into a 50-liter flask and cooled to 9.3° C. To compound 4 in the 50-liter flask was added triethylamine (0.864 kg, 8.537 mole), followed by 4-dimethylaminopyridine (DMAP) (0.087 kg, 0.7114 mol) and 2,6-dichlorobenzoyl chloride (1.34 kg, 6.40 mol) in 2-methyl-THF (25 L) over a period of 2 hrs. The reaction was quenched with methanol (0.30 L at room temperature and added an aqueous NaCl solution (12.5 L, 15%) and celite (0.5 kg). The mixture was stirred and filtered through celite. The filtrate was concentrated and added 5 volumes of heptanes. The resulting solution was stirred for about 1 hr and dried with sodium sulfate (1 kg) and filtered. Compound 5 was isolated by removing the solvents under vacuum. MS (ESI): M+H$^+$=524, 525.8, 527.8. $^1$H NMR (DMSO-d$_6$, δ ppm): 5.36 (2H, s), 7.01 (2H, m), 7.68 (3H, s), 8.34 (1H, brs), 8.61 (1H, brs), 8.72 (1H, d J=2.3 Hz).

Step 4: Preparation of (3-(3-amino-2,6-difluorobenzoyl)-5-(2-cyclopropylpyrimidin-5-yl)-1H-pyrrolo[2,3-b]pyridin-1-yl)(2,6-dichlorophenyl)methanone

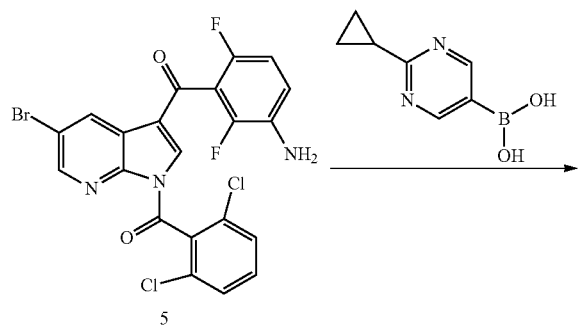

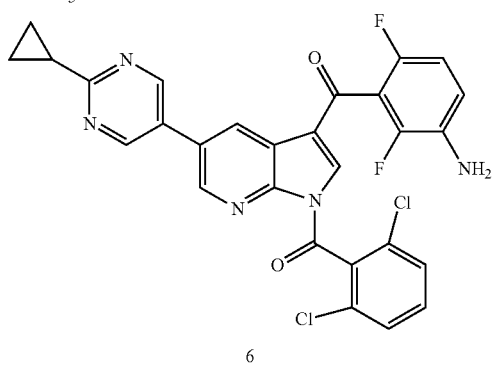

6

Compound 5 (40 g, 0.076 mole) and 2-cyclopropylpyrimidin-5-yl-5-boronic acid (Compound A) (23 g, 0.141 mole) in 2 methyltetrahydrofuran (2-MeTHF) (1,720 mL) which 8% sodium bicarbonate (sparged with nitrogen) and bis(triphenylphosphine)palladium(II) dichloride (1 g, 0.0014 mole) were added. The mixture was heated to reflux to give Compound 6 which was isolated, washed and dried. LCMS: m/z=564.0 (M+H)$^+$. $^1$H NMR (DMSO-d$_6$, δ ppm): 9.05 (s, 2H), 9.00 (s, 1H), 8.62 (s, 1H), 8.58 (s, 1H), 7.70 (m, 3H), 7.04 (m, 2H), 5.36 (br s, 2H), 2.30 (m, 1H), 1.16 (m, 4H).

Step 5: Preparation of (R)-N-(3-(5-(2-cyclopropylpyrimidin-5-yl)-1-(2,6-dichlorobenzoyl)-1H-pyrrolo[2,3-b]pyridine-3-carbonyl)-2,4-difluorophenyl)-3-fluoropyrrolidine-1-sulfonamide

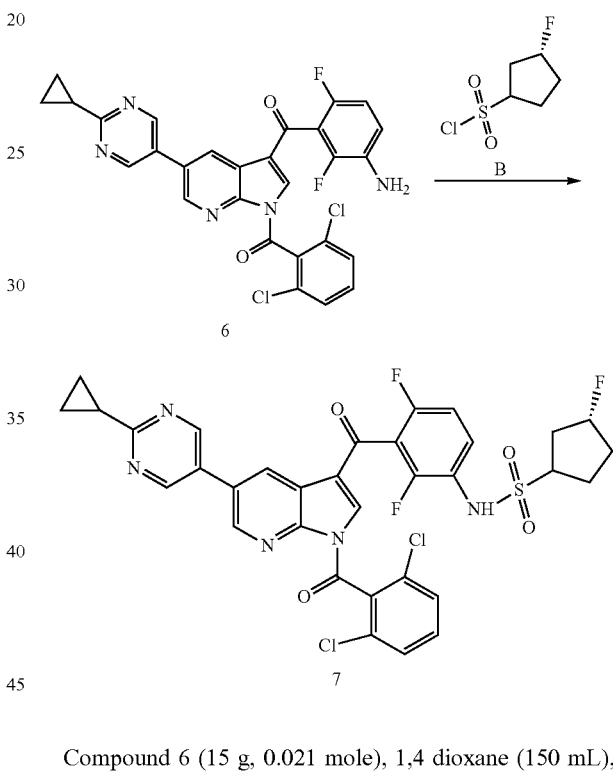

Compound 6 (15 g, 0.021 mole), 1,4 dioxane (150 mL), pyridine (15 mL, 49.6 mole), and Compound B (3-R-fluropyrrolidine sulfonyl chloride, 11.81 g, 0.063 mole) were charged to a flask. The reaction was stirred at room temperature and then heated to 50° C. and allowed to react overnight. Then charged to the reaction flask were ethyl acetate (60 mL) and water (60 mL). The organic layer was separated, washed, treated with activated carbon (Darco KG-B, 2.25 g) and filtered through a celite pad to yield Compound 7. $^1$H NMR (DMSO-d$_6$, δ ppm): 9.70 (s, 1H), 9.02 (s, 2H), 8.81 (m, 2H), 8.57 (m, 2H), 7.71 (m, 2H), 7.38 (m, 2H), 5.24-5.37 (2s, 1H), 3.31-3.42 (m, 4H), 2.05-2.29 (m, 3H), 1.12 (m, 4H).

Compound B was obtained by combining commercially available 3-R-fluoropyrrolidine HCl salt (20 kg, 159.3 mole) and commercially available sulfuryl chloride (21 kg, 155.6 mole) in a solution of dichloromethane (293 kg) and triethylamine (32 kg) to yield (R)-3 fluoropyrrolidine sulfonyl chloride (Compound B).

Step 6: Preparation of (R)-N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide

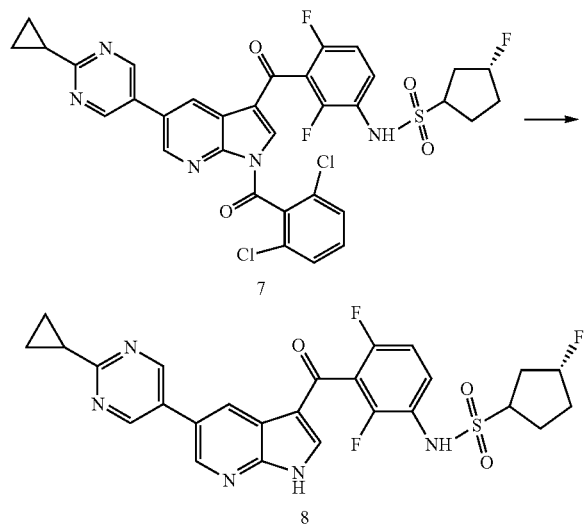

Compound 7 (26.9 kg) was dissolved in tetrahydrofuran (95.8 kg) and 7N ammonia in methanol (50.2 kg) was added to the reaction mixture. Once the reaction was deemed complete by HPLC, Compound 8 was isolated by solvent exchange with dichloromethane. Compound 8 was dissolved in tetrahydrofuran, filtered and concentrated, and the isolated material was purified, isolated and triturated in WFI (Water for Injection) (17.8 kg, 87% yield).

Example 2: Manufacturing Process of Solid Dispersion of Amorphous Compound I Using Hot Melt Extrusion (HME)

A representative batch formula for Compound I is as shown below in Table 1.

TABLE 1

Solid Dispersion Formulation of Compound I

| Component | Function | % w/w |
| --- | --- | --- |
| Compound I | Active ingredient | 7.95 |
| Colloidal silicon dioxide | Glidant | 1.0 |
| Copovidone | Solubilizing Agent | 37.1 |
| Croscarmellose sodium | Disintegrant | 3.0 |
| Crospovidone | Disintegrant | 7.0 |
| Magnesium stearate[a] | Lubricant | 1.0 |
| Mannitol | Filler/Binder | 7.0 |
| Microcrystalline cellulose | Filler/Binder | 8.0 |
| Poloxamer 407 | Solubilizing Agent | 6.0 |
| Polyethylene glycol 400 | Solubilizing Agent | 7.95[b] |
| Sodium bicarbonate | Disintegrant | 8.0 |
| Sodium chloride | Osmogen | 4.0 |
| Sodium lauryl sulfate | Surfactant | 2.0 |
| Total | | 100 |

[a]Obtained from a non-bovine source.
[b]Amount may be adjust based on Compound I/Copovidone blend obtained during the extrudate milling process.

A process flow diagram for manufacturing solid dispersion of amorphous Compound I is provided in FIG. 1.

Description of Manufacturing Process and Process Controls for Hot Melt Extrusion Formulation (HME)

Hot Melt Extrusion Formulations

Solid dispersions of amorphous Compound I can be formulated using a hot-melt extrusion process (referred to herein as formulation, HME solid dispersion formulation, or HME formulation) comprising hot-melt extrusion, milling, blending, and optionally tableting. Multiple hot-melt extrusion and milling batches may be combined for blending and tableting to make larger batch sizes.

Hot-Melt Extrusion and Milling

Step 1. Suitable amounts of Compound I (about 7.95 w/w % of solid dispersion formulation) and copovidone (about 37.1 w/w % of solid dispersion formulation) were added to a V-blender.

Step 2. The contents from 1 were blended for about 5 minutes and the contents were then screen sieved.

Step 3. The contents from step 2 were transferred back to the V-blender and blended for about 10 minutes.

Step 4. A suitable amount of polyethylene glycol 400 (PEG400) (about 7.95 w/w % of solid dispersion formulation) was weighed in a suitable container. An additional about 20 g of PEG 400 was used for setting up the extruder, and this additional about 20 g of PEG 400 was not part of the formulation.

Step 5. An extruder was set up using appropriate set points and using the about 20 g of PEG 400 from Step 4 to adjust the flow rate.

Step 6. The Compound I Blend from Step 3 was added to a feed hopper and the extrusion process was initiated. The extrusion parameters were adjusted and monitored as necessary.

Step 7. The resulting pelletized extrusion was collected and weighed.

Step 8. The pelletized extrusion was placed in a suitable container.

Blending

Step 9. The following materials were weighed and screen/milled: Colloidal Silicon Dioxide (about 1.0 w/w % of solid dispersion formulation), Croscarmellose Sodium (about 3.0 w/w % of solid dispersion formulation), Crospovidone (about 7.0 w/w % of solid dispersion formulation), Mannitol (about 7.0 w/w % of solid dispersion formulation), Microcrystalline Cellulose (about 8.0 w/w % of solid dispersion formulation), Poloxamer 407 (about 6.0 w/w % of solid dispersion formulation), Sodium Bicarbonate (about 8.0 w/w % of solid dispersion formulation), Sodium Chloride (about 4.0 w/w % of solid dispersion formulation), and Sodium Lauryl Sulfate (about 2.0 w/w % of solid dispersion formulation).

Step 10. The milled extrudate from Step 8 and the screened excipients from step 9, were added to a bin-blender and blended for about 30 minutes.

Step 11. Magnesium stearate (about 1.0 w/w % of solid dispersion formulation) was weighed out and screened.

Step 12. The magnesium stearate was added to the contents of the bin-blender from step 10 and blended for about 5 minutes.

Step 13. The blend from step 12 was placed in a suitable, labeled container.

Tableting

Step 14. The blend from step 13 was transferred to a rotary tablet press hopper.

Step 15. A tablet press was set up to yield target tablet weight, hardness, and friability.

Step 16. The blend was tableted, and the tablet weight and hardness were monitored about every 15 minutes.

Step 17. Metal check and weight sort were performed on the tablets from step 16.

Step 18. The resulting tablets from step 17 can then be packaged as required.

Example 3: Manufacturing Process of Solid Dispersion of Amorphous Compound I Using Spray Dry Dispersion (SDD)

TABLE 2

Spray Dry Dispersion Formulation of Compound I

| Component | % w/w (solids) | Intra-granular % w/w | Extra-granular % w/w |
|---|---|---|---|
| Spray Dried Dispersion (Initial Blend) | | | |
| Compound I | 25 | 25 | |
| Hypromellose acetate succinate (HMPCAS—HG) | 70 | 70 | |
| Sodium lauryl sulfate | 5.0 | 5 | |
| Acetone:water (90:10) | — | | |
| Subtotal: | 100 | | |
| Spray Dried Dispersion Final Blend | | | |
| Spray Dried Dispersion (Compound I, Hypromellose acetate succinate, sodium lauryl sulfate) | 60 | | |
| Colloidal silicon dioxide | 2.0 | | |
| Croscarmellose sodium | 6.0 | 3 | 3 |
| Mannitol | 16.00 | | |
| Microcrystalline cellulose | 15.25 | 10.25 Avicel PH-105 | 5 Avicel PH-101 |
| Sodium Stearyl Fumarate | 0.75 | 0.50 | 0.25 |
| Subtotal: | 100.00 | | |

<sup>a</sup>Removed during processing.
<sup>b</sup>Approximate tablet yield: weight of blend per tablet maybe adjusted based on assay of final blend uniformity sampling to target 100% label claim in the finished drug product.

A process flow diagram for manufacturing solid dispersions of amorphous Compound I by spray dry dispersion, and tables thereof, is provided in FIG. 2.

Description of Manufacturing Process and Process Controls

The SDD formulation of Compound I can be manufactured using spray dried dispersion approach that includes spray dry dispersion to form an initial spray dry dispersion; and followed by dry granulation of the SDD and blending to make a spray dry dispersion final blend. The SDD final blend can then be tableted and packaged prior to administration to subjects.

Spray Dried Dispersion (Initial Blend)—60% w/w of Final Blend

Step 1. Spray solution solvents (Acetone and Water), HPMCAS-HG (70% w/w of Spray Dried Dispersion), sodium lauryl sulfate (SLS) (5% w/w of Spray Dried Dispersion), and Compound I (25% w/w of Spray Dried Dispersion) were weighed and put into a suitable containers.

Step 2. The SLS was slowly added into the spray solution of Step 1 while mixing, followed by Compound I, and mixing was continued until no visible particles were observed.

Step 3. During mixing, the HPMCAS-HG was slowly added and mixing continued until no solid particles were observed.

Step 4. The resulting solution was spray dried using a standard pharmaceutical grade spray dryer, such as MS-150.

Step 5. Following completion of spray drying, the Spray-Dried Dispersion (initial blend) was dried in an oven for about 8 hours and until the residual acetone was below ICH guidelines, 5000 ppm.

Step 6. The dried SDD from Step 5 was transferred and into appropriate containers with desiccants to protect from moisture.

Dry Granulation and Blending

Step 7. The SDD (60% w/w of Final Blend), and intra-granular excipients, were dispensed into appropriate containers. The intra-granular excipients employed were Sodium Stearyl Fumarate (0.50% w/w of Final Blend), Colloidal Silicon Dioxide (2% w/w of Final Blend), Croscarmellose sodium (3% w/w of Final Blend), Mannitol (16% w/w of Final Blend), and Microcrystalline Cellulose (10.25% w/w of Final Blend)

Step 8. The SDD and intra-granular excipients were added to a blender of an appropriate size and blended for 12±5 minutes.

Step 9. The blend was passed through a comil to improve blend uniformity and remove large particles.

Step 10. The Blend from step 9 was further blended and then discharged into appropriate container.

Step 11. The blend from step 10 was dry granulated to result in ribbons using an appropriate roller compactor, such as TFC-220 roller compactor or others, using selected process parameters (roll type, RPM and roll compaction force).

Step 12. The resulting ribbons from step 11 were milled using a comil to result in a free flowing granulation.

Step 13. Appropriate quantities of the extra-granular excipients were added (Sodium Stearyl Fumarate, microcrystalline cellulose, and Croscarmellose sodium) to the granulation and blend to obtain the blend for tablet compression.

Tableting and Packaging

A rotary tablet press was set up to yield target tablet weight, hardness, and friability.

The final blend was tableted, and the tablet weight and hardness were monitored at initial startup and at about 15 minute intervals.

Metal check and weight sorting were performed for the tablets.

TABLE 3

Process Controls-Spray Dry Dispersion

| Step | Process | Test | Sample Interval | Acceptance Criteria/Descriptions |
|---|---|---|---|---|
| 5 | Spray Drying | pXRD | At end | Substantially amorphous |
| 6 | Drying | Residual solvent | End of drying | Residual Solvent Acetone ≤ 5000 ppm |
| 17, 18 | Tableting | Tablet weight | Initial set-up, during, and end of compression | 930 mg to 1070 mg |
| 17 | Tableting | Friability | Initial set-up of compression | NMT 1% weight loss | pXRD = powder X-Ray Diffraction

Example 4: Comparative Study of Crystalline Compound I and Solid Dispersion of Amorphous Compound I The following table 4 provides the compositions of three formulations, namely the crystalline Compound I formulation, solid (spray dry) dispersion of amorphous Compound I and solid (hot melt extrusion) dispersion of Compound I and their comparisons.

TABLE 4

Compositions of Three Formulations

| Formulation Dosage Strength | | Crystalline Compound I Formulation 150 mg capsule | | Solid Dispersion of Amorphous Compound I 75 mg tablet Hot Melt Extrusion | | Solid Dispersion of Amorphous Compound I 150 mg tablet Spray Dry Dispersion | |
|---|---|---|---|---|---|---|---|
| Method of Manufacture | | % | mg/ | % | mg/ | % | mg/ |
| Component | Function | w/w | capsule | w/w | tablet | w/w | tablet |
| Compound I | Active ingredient | 36.77 | 150.0 | 7.95 | 75.0 | 15.0 | 150.0 |
| Colloidal silicon dioxide[c] | Glidant | — | — | 1.0 | 9.43 | 2.0 | 20.0 |
| Copovidone[c] | Binder, solubilizing agent | 10.0 | 40.8 | 37.1 | 350.0 | — | — |
| Croscarmellose sodium[c] | Disintegrant | — | — | 3.0 | 28.3 | 6.0 | 60.0 |
| Crospovidone[c] | Disintegrant | — | — | 7.0 | 66.04 | — | — |
| Hypromellose Acetate Succinate[c] | Dispersion polymer | — | — | — | — | 42.0 | 420.0 |
| Magnesium stearate[a,c] | Lubricant | 1.0 | 4.08 | 1.0 | 9.43 | — | — |
| Mannitol[c] | Diluent Filler/Binder | 37.23[b] | 151.9 | 7.0 | 66.04[b] | 16.0 | 160.0 |
| Microcrystalline cellulose[c] | Filler/Binder | — | — | 8.0 | 75.47 | 15.25 | 152.5 |
| Poloxamer 407[c] | Solubilizing agent | 10.0 | 40.8 | 6.0 | 56.6 | — | — |
| Polyethylene glycol 400[c] | Solubilizing agent | — | — | 7.95 | 75.0 | — | — |
| Sodium bicarbonate[c] | Disintegrant | — | — | 8.0 | 75.47 | — | — |
| Sodium chloride[c] | Osmogen | — | — | 4.0 | 37.74 | — | — |
| Sodium lauryl sulfate[c] | Surfactant | — | — | 2.0 | 18.87 | 3.0 | 30.0 |
| Sodium Stearyl Fumarate[c] | Lubricant | — | — | — | — | 0.75 | 7.5 |
| Vitamin E tocopheryl polyethylene glycol succinate (Vitamin E TPGS)[c] | Solubilizing agent | 5.0 | 20.4 | — | — | — | — |
| Total Fill Weight | | 100.0 | 408.0 | 100.0 | 943.3 | 100.0 | 1000.0 |

USP = United States Pharmacopeia convention;
NF = National Formulary
[a]Obtained from a non-bovine source.
[b]Amount of mannitol is adjusted based on amount of Compound I.
[c]Quality Standard is USP-NF.

Crystalline Formulation of Compound I

A formulation of compound I (described in Table 4) was developed using a crystalline formulation approach. Solubilizing agents Vitamin E TPGS (d-α-tocopheryl polyethylene glycol succinate) and Poloxamer 407 were added to increase the solubility and bioavailability. Additional compendial pharmaceutical excipients were included to perform their standard functions.

The crystalline formulation was manufactured as an immediate release 150 mg capsule formulation and was used in a human clinical study. The maximum exposure achieved in this study, $AUC_t$=2500 ng·hr/mL Table 5), was significantly lower than the expected target efficacious exposure (74000 ng·hr/mL). This result was unexpected provided that there was significantly better preclinical data that led to initiation of this clinical study in humans using this crystalline formulation. This clinical study in humans was discontinued based on this unexpected outcome, and the 150 mg crystalline capsule was no longer used.

TABLE 5

Pharmacokinetic Parameters of Crystalline Formulation of Compound I

| Daily Dose | Number of Patients | C1D1 | | | C1D15 | | |
|---|---|---|---|---|---|---|---|
| | | $T_{max}$ (hr) | $C_{max}$ (ng/mL) | $AUC_\tau$ (ng · hr/mL) | $T_{max}$ (hr) | $C_{max}$ (ng/mL) | $AUC_\tau$ (ng · hr/mL) |
| 900 mg (450 mg BID) | 3 | 2.3 | 430 | 2000 | 1.7 | 420 | 2200 |
| 1800 mg (900 mg BID) | 1 | 2 | 550 | 1900 | 1 | 660 | 2500 |

C1D1 = Cycle 1, Day 1;
C1D15 = Cycle 1, Day 15

Solid Dispersion Formulation of Amorphous Compound I (75 mg Tablet)

Formulations using amorphous solid dispersion of Compound I were developed to overcome the unexpected low exposure of the crystalline capsule formulation observed in humans. A solid dispersion formulation was developed using a hot melt extrusion (HME) process.

The 75 mg tablet formulation (described in Table 4) was made using the hot melt extrusion (HME) process described in this disclosure. This 75 mg tablet was used in human clinical studies (single-dose study in healthy volunteers) and (repeat-dose study in cancer patients). The pharmacokinetics (PK) parameters from the two studies are summarized in Table 6 and Table 7. A dose-proportional increase in exposure, as represented by both $C_{max}$ and AUC, was observed following a single dose of Compound I administered as 75 mg HME tablet (Table 6). Following repeat dosing, the steady state exposure at the highest dose evaluated (900 mg BID), $AUC_t$=68700 ng·hr/mL, approached the target efficacious exposure (Table 7).

TABLE 6

Single-dose Pharmacokinetic Parameters of Compound I in Humans

| | Geometric Mean (CV %) | | | |
|---|---|---|---|---|
| Parameter | Compound I 150 mg (N = 6) | Compound I 300 mg (N = 5) | Compound I 450 mg (N = 6) | Compound I 900 mg (N = 6) |
| $t_{max}{}^a$ (hr) | 2.00 (1.00-3.00) | 2.00 (1.00-2.00) | 1.00 (1.00-2.03) | 1.00 (1.00-2.00) |
| $C_{max}$ (ng/mL) | 2070 (37.8) | 4180 (27.7) | 7500 (64.3) | 13300 (67.8) |
| $AUC_{0-12}$ (ng · hr/mL) | 7240 (41.4) | 12100 (51.6) | 21000 (61.7) | 37500 (57.2) |
| $AUC_{0-24}$ (ng · hr/mL) | 7720 (41.6) | 12600 (53.5) | 21800 (61.7) | 39200 (55.1) |
| $AUC_{0-\infty}$ (ng · hr/mL) | 7610 (46.9) | 13200 (56.5) | 22400 (62.5) | 40400 (55.8) |
| $t_{1/2}$ (hr) | 8.18 (89.4) | 9.56 (139.5) | 8.36 (69.3) | 9.12 (81.1) |
| CL/F (L/hr) | 19.7 (46.9) | 22.7 (56.5) | 20.1 (62.5) | 22.3 (55.8) |
| Vz/F (L) | 233 (65.7) | 313 (118.1) | 243 (79.1) | 293 (53.6) |

$^a$Median (minimum-maximum).

TABLE 7

Repeat-dose Pharmacokinetic Parameters of Compound I in Humans

| Daily Dose | Number of Patients | *C1D1 $C_{max}$ (ng/mL) | *C1D1 $AUC_{0-12}$ (ng · hr/mL) | *C1D15 $C_{max}$ (ng/mL) | *C1D15 $AUC_{0-12}$ (ng · hr/mL) |
|---|---|---|---|---|---|
| 900 mg (450 mg BID) | 8 | 12400 | 43200 | 14000 | 48000 |
| 1800 mg (900 mg BID) | 3 | 15800 | 45700 | 22500 | 68700 |

*C1D1 = Cycle 1, Day 1, C1D15 = Cycle 1, Day 15

One limitation of the 75 mg HME tablet was the high pill burden at the desired dose (900 mg BID).

Solid Dispersion Formulation of Amorphous Compound I (150 mg Tablet)

A second amorphous formulation using spray-dried dispersion technology was developed as a 150 mg tablet to reduce pill burden and improve tablet physical properties over the 75 mg tablet prepared by HME. A number of SDD-based tablet formulations were screened in pre-clinical studies. The solid dispersion of amorphous Compound I (150 mg tablet), as described in Table 4, was selected based on processability, tablet physicochemical properties, and bioavailability in animals. In single-dose PK studies in dogs, the two solid dispersion amorphous formulations (HME and SDD) resulted in similar exposures (Table 8).

TABLE 8

Pharmacokinetics of Compound I at 45 mg/kg in Dogs with Two Different Solid Dispersion Amorphous Formulations

| Formulation | | $t_{max}$ (hr) | $C_{max}$ (ng/mL) | $AUC_{0-24}$ (ng · hr/mL) | $AUC_\infty$ (ng · hr/mL) | Vz/F (L/kg) | Cl/F (mL/min/kg) | $t_{1/2}$ (hr) | $MRT_\infty$ (hr) |
|---|---|---|---|---|---|---|---|---|---|
| HME Compound I | Mean | 1.67 | 30700 | 89800 | 90000 | 2.49 | 10.3 | 2.97 | 3.14 |
| | SE | 0.333 | 6750 | 24700 | 24800 | 0.67 | 3.66 | 0.371 | 0.325 |
| SDD Compound I | Mean | 2 | 28400 | 89500 | 89800 | 3.68 | 11.9 | 3.28 | 3.43 |
| | SE | 0 | 4420 | 32200 | 32200 | 1.85 | 5.21 | 0.732 | 0.372 |

The SDD tablet formulation resulted in both reduced patient pill burden, from 24 to 12 daily tablets, by increasing unit dosage strength from 75 mg to 150 mg, and also in improved tablet physical properties.

Example 5: Pharmacokinetic Profile of Compound I (HME) with and without CYP Inhibitors CYP reaction phenotyping analysis identified CYP3A4 as the main cytochrome P450 enzyme responsible for metabolism of Compound I. It was observed in Phase I clinical trials that the addition of broad-spectrum CYP inhibitor ABT or selective CYP3A4 inhibitor cobicistat blocked the metabolism of Compound I.

A Phase 1 open-label two-part study was conducted to: (i) evaluate the pharmacokinetics (PK) and safety of single ascending doses of Compound I; and (ii) assess the effect of the CYP3A4 inhibitor cobicistat on the PK of Compound I in healthy subjects. A total of 40 adult subjects with a mean age of 37 years were enrolled. Part A enrolled subjects into four single dose cohorts of Compound I ranging from 150 to 900 mg, and the PK data were evaluated to select the most appropriate dose level to use in Part B (900 mg). In Part B, advancing subjects from the 900 mg cohort in Part A completed a 7-day washout and then received a single 150 mg oral dose of cobicistat on Days 1 through 6 plus a single 900 mg oral dose of Compound I on Day 3; new subjects added to this cohort received a second dose of Compound I alone on Day 13. An additional cohort received a single 300 mg oral dose of Compound I on Day 1, a single 150 mg oral dose of cobicistat on Days 5 through 10, and a single 300 mg oral dose of Compound I coadministered with cobicistat on Day 7. All doses of each drug were administered in the fasted state. This study used an amorphous solid dispersion formulation of Compound I produced with a hot-melt extrusion (HME) process. The PK parameters are summarized in Tables 9A and 9B.

TABLE 9A

Pharmacokinetic Profile of Compound I

| PK Parameters | Geometric Mean (% CV) Part A | | | |
|---|---|---|---|---|
| | Compound I 150 mg (N = 6) | Compound I 300 mg (N = 5) | Compound I 450 mg (N = 6) | Compound I 900 mg (N = 6) |
| $AUC_{0-24}$ (ng · hr/mL) | 7720 (41.6) | 12600 (53.5) | 21800 (61.7) | 39200 (55.1) |
| $AUC_{0-t}$ (ng · hr/mL) | 7870 (44.1) | 12900 (56.0) | 22100 (62.6) | 40000 (55.8) |

TABLE 9A-continued

Pharmacokinetic Profile of Compound I

| PK Parameters | Geometric Mean (% CV) Part A | | | |
|---|---|---|---|---|
| | Compound I 150 mg (N = 6) | Compound I 300 mg (N = 5) | Compound I 450 mg (N = 6) | Compound I 900 mg (N = 6) |
| $AUC_{0-\infty}$ (ng · hr/mL) | 7610 (46.9) | 13200 (56.5) | 22400 (62.5) | 40400 (55.8) |
| $C_{max}$ (ng/mL) | 2070 (37.8) | 4180 (27.7) | 7500 (64.3) | 13300 (67.8) |
| $T_{max}$ (hr)[a] | 2.0 (1.0-3.0) | 2.0 (1.0-2.0) | 1.0 (1.0-2.0) | 1.0 (1.0-2.0) |
| $t_{1/2}$ (hr) | 8.18 (89.4) | 9.56 (139.5) | 8.36 (69.3) | 9.12 (81.1) |

[a]$T_{max}$ data presented as median (minimum-maximum).

TABLE 9B

Pharmacokinetic Profile of Compound I

Geometric Mean (% CV)
Part B

| PK Parameters | Compound I 150 mg (N = 6) | Compound I 900 mg Cobicistat 150 mg (N = 12) | Compound I 900 mg (N = 10) | Compound I 300 mg + Cobicistat 150 mg (N = 8) | Compound I 300 mg (N = 8) |
|---|---|---|---|---|---|
| $AUC_{0-24}$ (ng·hr/mL) | 7720 (41.6) | 128000 (36.0) | 34100 (60.5) | 39900 (57.6) | 15800 (31.2) |
| $AUC_{0-t}$ (ng·hr/mL) | 7870 (44.1) | 132000 (36.6) | 34800 (60.9) | 41700 (62.2) | 16200 (33.2) |
| $AUC_{0-\infty}$ (ng·hr/mL) | 7610 (46.9) | 133000 (36.7) | 35200 (60.7) | 42100 (61.9) | 16400 (33.6) |
| $C_{max}$ (ng/mL) | 2070 (37.8) | 31000 (32.6) | 11400 (65.4) | 8490 (45.1) | 4840 (24.2) |
| $T_{max}$ (hr)$^a$ | 2.0 (1.0-3.0) | 2.0 (1.0-3.0) | 2.0 (1.0-2.0) | 2.0 (2.0-3.0) | 2.0 (1.0-2.0) |
| $t_{1/2}$ (hr) | 8.18 (89.4) | 9.67 (60.9) | 8.94 (108.0) | 8.67 (61.2) | 9.96 (84.9) |

In Part A, Compound I showed linear PK when administered as single ascending doses under fasted conditions. Exposure increased dose proportionally over the studied dose range of 150 to 900 mg. Part B followed a 2-sequence crossover design to evaluate the effect of cobicistat (a CYP3A4 inhibitor) on the PK of a single oral dose of Compound I in the fasted state. Cobicistat co-administration increased Compound I exposure. Compared with Compound I administered alone, mean AUC0–t and AUC0 ∞ increased 2.6-fold (300 mg level) and 3.8-fold (900 mg level), and mean $C_{max}$ increased 1.8-fold (300 mg level) and 2.7-fold (900 mg level).

Example 6: Pharmacokinetic Profiles of Compound I (HME) & (SDD) with CYP Inhibitors An amorphous solid dispersion formulation of Compound I using spray-dried dispersion technology was developed to overcome the pill burden, improve physical properties, and enable the drug to be administered as an oral suspension.

The 150 mg tablet formulation (described in Table 4) was made using the spray dry dispersion (SDD) process described in this disclosure. This 150 mg tablet was used in a human clinical study (repeat-dose study in cancer patients). The resulting Day 1 $AUC_{0-12}$ (161,000 ng·hr/mL, N=4) of Compound I [SDD] 1350 mg BID+cobicistat is within the standard bioequivalence limit of 80-125% from the target recommended phase 2 dose (RP2D) exposure ($AUC_{0-12}$=149,000 ng·hr/mL). The steady state (Day 15) $AUC_{0-24}$ (630,000 ng·hr/mL, N=3) of Compound I [SDD] 1350 mg BID+cobicistat is about 1.8× above the Compound I [HME] RP2D steady state exposure ($AUC_{0-24}$=318,000 for dose escalation/N=6 and 324,000 ng·hr/mL for RP2D extension/N=22). The pharmacokinetics (PK) parameters from the study are summarized in Table 10. A dose-proportional increase in exposure from 900 mg to 2700 mg, as represented by both $C_{max}$ and AUC, was observed following a single dose of Compound I administered as 150 mg SDD tablets (Table 10). Following repeat dosing, the steady state exposure at the highest dose evaluated (1350 mg BID), $AUC_t$=315,000 ng·hr/mL, approached the target efficacious exposure (Table 10).

TABLE 10

Repeat-dose Pharmacokinetic Parameters of Compound I in Humans

| | | *C1D1 | | *C1D15 | | |
|---|---|---|---|---|---|---|
| Daily Dose | Number of Patients | $C_{max}$ (ng/mL) | $AUC_{0-12}$ (ng·hr/mL) | $C_{max}$ (ng/mL) | $AUC_{0-12}$ (ng·hr/mL) | $AUC_{0-24}$ (ng·hr/mL) |
| 1800 mg (900 mg BID) HME + Cobicistat | 6 | 38,600 | 149,000 | 31,300 | 159,000 | 318,000 |
| 900 mg (450 mg BID) SDD + Cobicistat | 2 | 9,600 | 43,800 | 13,000 | 80,800 | 161,600 |
| 2700 mg (1350 mg BID) SDD + Cobicistat | 4/2 | 24,500 | 161,000 | 46,200 | 315,000 | 630,000 |

*C1D1 = Cycle 1, Day 1; C1D15 = Cycle 1, Day 15

What is claimed is:

1. A spray dry dispersion formulation comprising Compound I having the formula:

Compound I wherein Compound I is substantially amorphous, and further wherein Compound I is molecularly dispersed within a polymer matrix formed by hydroxypropylmethyl cellulose acetate succinate (HPMCAS) in its solid state;
   a glidant ranging from about 1.5% w/w to about 2.5% w/w;
   a disintegrant ranging from about 5% w/w to about 7% w/w;
   a filler/binder ranging from about 29% w/w to about 33% w/w;
   a lubricant ranging from about 0.7% w/w to about 0.8% w/w; and
   a surfactant;
   wherein the glidant is colloidal silicon dioxide; the disintegrant is croscarmellose sodium; the filler/binder are mannitol and microcrystalline cellulose, and the lubricant is sodium stearyl fumarate; and
   wherein the combination of Compound I, HPMCAS and surfactant ranges from about 56.7% w/w to about 63.8% w/w of the formulation.

2. The formulation according to claim 1, wherein the HPMCAS is HPMCAS-LF, HPMCAS-MF, HPMCAS-HF, HPMCAS-LG, HPMCAS-MG or HPMCAS-HG.

3. The formulation according to claim 1, wherein the HPMCAS is HPMCAS-HG.

4. The formulations according to claim 1, wherein the weight ratio of Compound I to HPMCAS ranges from about 1:2.5 to about 1:3.5.

5. The formulation according to claim 1, wherein the weight ratio of Compound I to HPMCAS ranges from about 1:2.6 to about 1:2.9.

6. The formulation according to claim 1, wherein the surfactant is sodium lauryl sulfate.

7. The formulation according to claim 1, wherein the weight ratio of mannitol to microcrystalline cellulose ranges from about 2:3 to about 3:2.

8. The formulation according to claim 1, wherein the weight ratio of mannitol to microcrystalline cellulose ranges from about 1:1:1:0 to about 1.0:1.1.

9. The formulation according to claim 1, wherein the formulation is in a tablet form suitable for oral dosage.

10. The formulation according to claim 9, wherein the tablet is suspended in water or a water containing solvent.

11. A method of treating a BRAF mutation related disease or condition, comprising administering to a subject in need thereof a therapeutically effective amount of a formulation according to claim 1, wherein the BRAF mutation related disease or condition is melanoma, colorectal cancer, papillary thyroid cancer, papillary craniopharyngiomas, anaplastic thyroid cancer, ovarian cancer, non-small-cell lung cancer, gastric cancer, cholangiocarcinoma, Barrett's esophageal cancer, head and neck cancer, hepatocellular carcinoma, breast cancer, Langerhan's cell histiocytosis, gastrointestinal stromal cell tumours (GIST), multiple myeloma, pediatric astrocytomas, pleomorphic xanthoastrocytomas, chronic myeloid leukemia, acute myelomonocytic leukemia, biphenotypic B myelomonocytic leukemia, acute myeloid leukemia, hairy cell leukemia, nevi, Erdheim-Chester Disease, malignant peripheral nerve sheath tumor, inflammatory and autoimmune disease, tenosynovial giant cell tumor, pigmented villonodular synovitis, giant cell tumor of tendon sheath, giant cell tumor of bone, cervical cancer, endometrial cancer, germ cell tumors, prostate cancer, bladder cancer, myopericytoma, metanephric adenoma, pancreatic neoplasms, neuroendocrine tumors, endocrine tumors, adrenal tumors, adrenal medullary tumors, cystadenocarcinoma of the parotid, glioblastoma multiforme, bile duct cancer including bile duct adenoma, choloangiocarcinoma, B-cell chronic lymphoproliferative disorder, dendritic cell sarcomas, histiocytic sarcomas, or lymphoma.

12. The method according to claim 11, wherein the BRAF mutation related disease or condition is hepatocellular carcinoma, Langerhan's cell histiocytosis, Erdheim Chester Disease, gastrointestinal stromal cell tumours, hairy cell leukemia, hairy cell leukemia, melanoma, colorectal cancer, papillary thyroid cancer, anaplastic thyroid cancer, ovarian cancer, non-small-cell lung cancer, glioblastoma multiforme, prostate cancer, gastric cancer, cholangiocarcinoma, or Barrett's esophageal cancer.

13. The method according to claim 11, further comprising co-administering to said subject a CYP inhibitor.

14. The method according to claim 13, wherein the CYP inhibitor is CYP3A inhibitor.

15. The method according to claim 14, wherein the CYP3A inhibitor is boceprevir, cobicistat, conivaptan, danoprevir and ritonavir, elvitegravir and ritonavir, grapefruit juice, indinavir and ritonavir, itraconazole, ketoconazole, lopinavir and ritonavir, posaconazole, ritonavir, saquinavir and ritonavir, telaprevir, tipranavir and ritonavir, troleandomycin, voriconazole, clarithromycin, diltiazem, idelalisib, nefazodone, nelfinavir, paritaprevir and ritonavir and ombitasvir, or dasabuvir.

16. The method according to claim 15, wherein the CYP3A inhibitor is cobicistat.

17. The formulation of claim 1, comprising:
   about 15% w/w of Compound I;
   about 42% w/w of HPMCAS;
   about 2% w/w of colloidal silicon dioxide;
   about 6% w/w croscarmellose sodium;
   about 16% w/w mannitol;
   about 15.25% w/w microcrystalline cellulose;
   about 0.75% w/w sodium stearyl fumarate; and
   about 3% w/w sodium lauryl sulfate.

18. The formulation of claim 9, wherein the tablet contains 75-150 mg of Compound I.

19. The formulation of claim 9, wherein the tablet contains 150 mg of Compound I.

* * * * *